US012675151B2

(12) United States Patent
Chen et al.

(10) Patent No.: US 12,675,151 B2
(45) Date of Patent: Jul. 7, 2026

(54) DEFIBRILLATION DEVICE AND MEDICAL DEVICE

(71) Applicant: SHENZHEN MINDRAY BIO-MEDICAL ELECTRONICS CO., LTD., Shenzhen (CN)

(72) Inventors: Dabing Chen, Shenzhen (CN); Wenbin Wu, Shenzhen (CN); Runping Zou, Shenzhen (CN); Li Xu, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 149 days.

(21) Appl. No.: 18/135,092

(22) Filed: Apr. 14, 2023

(65) Prior Publication Data

US 2023/0333629 A1 Oct. 19, 2023

Related U.S. Application Data

(63) Continuation-in-part of application No. PCT/CN2023/076919, filed on Feb. 17, 2023.

(30) Foreign Application Priority Data

Apr. 14, 2022 (CN) .......................... 202210390429.0
Dec. 2, 2022 (CN) .......................... 202211542587.X

(51) Int. Cl.
G06F 1/3296 (2019.01)
G16H 40/63 (2018.01)
(52) U.S. Cl.
CPC ........... *G06F 1/3296* (2013.01); *G16H 40/63* (2018.01)

(58) Field of Classification Search
CPC .. A61N 1/046; A61N 1/0563; A61N 1/37254; G06F 1/3296
See application file for complete search history.

(56) References Cited

U.S. PATENT DOCUMENTS 7,548,781 B2 * 6/2009 Vaisnys ................ A61N 1/3904
607/5
7,627,372 B2 * 12/2009 Vaisnys ................ A61N 1/3904
607/5
10,272,010 B2 * 4/2019 Freeman .............. A61N 1/3904

(Continued)

*Primary Examiner* — Brian T Misiura
(74) *Attorney, Agent, or Firm* — Morgan, Lewis & Bockius LLP

(57) ABSTRACT

Defibrillation devices provided embodiments of the present disclosure include a defibrillation component, a first processor, and a second processor. The defibrillation component performs a defibrillation task, the first processor acquires data from the defibrillation component and processes the data to obtain defibrillation data. The second processor acquires extension device data from an extension device. The second processor is connected with the first processor, and the second processor and the first processor are capable of transmitting preset information. In this defibrillation device, the defibrillation function is performed by the first processor, and the function of the extension device is performed by the second processor, such that the functional isolation between the defibrillation task and the extended task is achieved. The failure of the second processor or extension device does not affect the performance of the core defibrillation rescue function, so that the defibrillation device has high safety.

24 Claims, 9 Drawing Sheets

(56)            References Cited

U.S. PATENT DOCUMENTS

| | | | |
|---|---|---|---|
| 10,493,289 B2 * | 12/2019 | Volpe | G06F 1/3203 |
| 10,799,723 B2 * | 10/2020 | Patil | A61B 34/25 |
| 2006/0259080 A1 * | 11/2006 | Vaisnys | A61N 1/3904 |
| | | | 607/5 |
| 2007/0078487 A1 * | 4/2007 | Vaisnys | A61N 1/3904 |
| | | | 607/8 |
| 2009/0248100 A1 * | 10/2009 | Vaisnys | A61N 1/3975 |
| | | | 607/5 |
| 2014/0277227 A1 * | 9/2014 | Peterson | A61N 1/3987 |
| | | | 607/7 |
| 2015/0265844 A1 * | 9/2015 | Powers | A61N 1/3943 |
| | | | 607/6 |
| 2016/0325108 A1 * | 11/2016 | Volpe | A61B 5/352 |
| 2024/0100346 A1 * | 3/2024 | He | A61N 1/3904 |

* cited by examiner

100

100

140

110

400

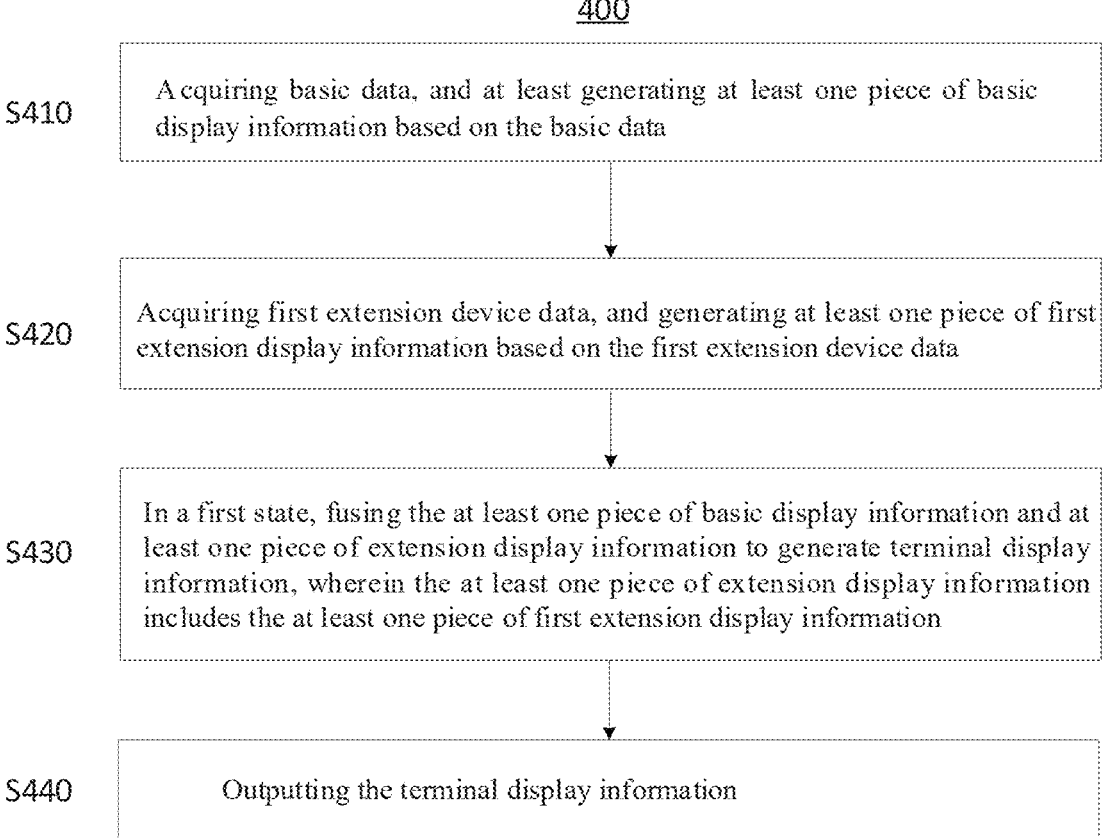

S410 — Acquiring basic data, and at least generating at least one piece of basic display information based on the basic data S420 — Acquiring first extension device data, and generating at least one piece of first extension display information based on the first extension device data S430 — In a first state, fusing the at least one piece of basic display information and at least one piece of extension display information to generate terminal display information, wherein the at least one piece of extension display information includes the at least one piece of first extension display information S440 — Outputting the terminal display information

FIG. 12

DEFIBRILLATION DEVICE AND MEDICAL DEVICE

CROSS-REFERENCE TO RELATED APPLICATIONS

This application is a continuation-in-part of International Application No. PCT/CN2023/076919, filed on Feb. 17, 2023, which claims priority to Chinese patent Application No. 202210390429.0, filed on Apr. 14, 2022. This application further claims priority to Chinese patent Application No. 202211542587X, filed on Dec. 2, 2022. The entire contents of each of the above-referenced applications are expressly incorporated herein by reference.

TECHNICAL FIELD

The disclosure relates to the technical field of medical device, and more particularly to a defibrillation device, a medical device and a display method for medical data.

BACKGROUND

Currently, more than two million people worldwide experience sudden death due to sudden cardiac arrest (SCA) every year. Electric shock defibrillation is the only one effective treatment for SCA. The vast majority of SCAs occur outside the hospital. Prehospital first aid is the main force for prehospital treatment, and defibrillation monitors are necessary device. In addition to prehospital first aid, there are also other different symptoms, such as internal bleeding, large-scale disaster sites, and other situations. With the continuous enrichment of treatment devices and the continuous improvement of treatment methods, prehospital first aid proposes higher requirements for multi-functional, portable defibrillation monitors, hoping that more functions can be integrated. At the same time, defibrillation device is a high-risk product which saves lives at critical times, the integration of more functions into it can have a negative effect on the reliability of the product.

SUMMARY

This disclosure provides a defibrillation device, aimed at solving a technical problem, such as reducing product reliability when expanding its function.

In a first aspect, an embodiment of the present disclosure provides a defibrillation device, including: a defibrillation component, which is configured to perform a defibrillation task; a first processor, which is configured to acquire data from the defibrillation component and process said data to obtain defibrillation data; and a second processor, which is configured to acquire extension device data from an extension device; wherein the second processor is connected with the first processor, and the second processor and the first processor are capable of transmitting preset information.

In some embodiments, the defibrillation device further includes a monitoring component, and the first processor is further configured to acquire data from the monitoring component and process said data to obtain monitoring data.

In some embodiments, the monitoring component includes at least one of: an ECG detection component, a blood oxygen detection component, and an NIBP detection component; and/or the defibrillation component includes a defibrillation function component and/or a pacemaker function component.

In some embodiments, when the first processor is in a working state, the second processor is in either one of at least two processor states, wherein the at least two processor states include a turn-off state or a low power consumption state, as well as a working state; wherein, when the second processor is in the working state, the second processor acquires the extension device data from the extension device.

In some embodiments, the first processor is further configured to switch the processor state of the second processor; and/or the second processor is further configured to switch the processor state of the second processor; and/or the defibrillation device further includes a third processor, which is configured to switch the processor state of the second processor.

In some embodiments, the processor state of the second processor is switched to the working state when at least one of the extension device, an extension function component, and an extension monitoring component satisfies a first extension start condition.

In some embodiments, the processor state of the second processor is switched according to the defibrillation data and/or monitoring data; wherein the monitoring data is obtained by the first processor, through processing data which is acquired from a monitoring component.

In some embodiments, the processor state of the second processor is switched to the working state when the defibrillation data and/or the monitoring data satisfy/satisfies a preset second extension start condition.

In some embodiments, the defibrillation device further includes a human-machine interaction component; wherein the processor state of the second processor is switched to the working state according to a processor start instruction and/or an extension start instruction, wherein the processor start instruction and/or the extension start instruction are/is acquired through the human-machine interaction component; wherein the processor start instruction is configured to control the second processor to switch to the working state, and the extension start instruction is configured to control the second processor to switch to the working state and to acquire the extension device data from the extension device which corresponds to the extension start instruction.

In some embodiments, the human-machine interaction component is further configured to output indication information when the defibrillation data and/or monitoring data satisfy/satisfies a preset indication condition: wherein the indication information is configured to indicate a user to operate to trigger the processor start instruction and/or the extension start instruction; wherein the monitoring data is obtained by the first processor, through processing data which is acquired from a monitoring component.

In some embodiments, a processor state of the second processor can be switched from a working state to a turn-off state or a low power consumption state; wherein, when the second processor is in the turn-off state or the low power consumption state, the second processor stops acquiring the extension device data from the extension device.

In some embodiments, the processor state of the second processor is switched to the turn-off state or the low power consumption state, when at least one of the extension device, an extension function component, and an extension monitoring component satisfies a first extension turn-off condition, and/or, when the defibrillation data and/or monitoring data satisfy/satisfies a preset second extension turn-off condition.

In some embodiments, the processor state of the second processor is switched to the turn-off state or the low power consumption state according to a turn-off instruction; wherein the turn-off instruction is acquired through a human-machine interaction component.

In some embodiments, when the second processor is in a working state, the second processor is further configured to transmit the acquired extension device data to the first processor; or when the second processor is in a working state, the second processor is further configured to process the acquired extension device data and then transmit the processed extension device data to the first processor.

In some embodiments, the first processor is further configured to output the defibrillation data and/or monitoring data through a human-machine interaction component, wherein the monitoring data is obtained by the first processor, through processing data which is acquired from a monitoring component; and when the second processor is in the working state, the first processor is further configured to output data which is transmitted by the second processor through the human-machine interaction component.

In some embodiments, the first processor is further configured to display the defibrillation data and/or the monitoring data through a display interface of the human-machine interaction component, and to superimpose the data transmitted by the second processor on a partial display area of the display interface when outputting the data transmitted by the second processor.

In some embodiments, when the second processor is in a working state, the first processor is configured to acquire an operation instruction for the extension device through a human-machine interaction component, and transmit the operation instruction for the extension device to the second processor; wherein the second processor is further configured to control the extension device to execute a corresponding extension task according to the operation instruction.

In some embodiments, when the second processor is in a working state, the first processor is configured to acquire an operation instruction for the extension device through a human-machine interaction component, and transmit the operation instruction for the extension device to the second processor; wherein the second processor is further configured to process the acquired extension device data from the extension device according to the operation instruction.

In some embodiments, the defibrillation device further includes a communication component; wherein the first processor is further configured to transmit the defibrillation data and/or monitoring data to the second processor; when the second processor is in a working state, the second processor is further configured to transmit the defibrillation data and/or monitoring data to a target device through the communication component; and/or when the second processor is in a working state, the second processor is further configured to transmit the acquired extension device data or processed extension device data to a target device through the communication component.

In some embodiments, the defibrillation device further includes a communication component; wherein the first processor is further configured to transmit the defibrillation data and/or monitoring data to the second processor; and when the second processor is in a working state, the second processor is further configured to transmit the defibrillation data and/or the monitoring data, and the acquired extension device data or processed extension device data to a target device through the communication component.

In some embodiments, when the second processor is in the working state, the second processor is further configured to generate target visual information according to the defibrillation data and/or the monitoring data, as well as, the acquired extension device data or the processed extension device data, and to transmit the target visual information to the target device through the communication component.

In some embodiments, the defibrillation device further includes an ultrasonic device and/or a laryngoscope device; wherein the second processor is further configured to acquire ultrasonic data and/or laryngoscope data from the ultrasonic device and/or the laryngoscope device.

In some embodiments, the ultrasonic data is ultrasonic image data, and/or the laryngoscope data is laryngoscope image data; when the second processor is in a working state, the second processor is further configured to transmit the ultrasonic image data and/or the laryngoscope image data to the first processor, so as to display an ultrasonic image and/or a laryngoscope image through a human-machine interaction component; and/or when the second processor is in a working state, the second processor is further configured to transmit the ultrasonic image data and/or the laryngoscope image data to a target device through a communication component.

In some embodiments, when the second processor is in a working state, the second processor is further configured to process the ultrasonic data and/or the laryngoscope data to generate ultrasonic image data and laryngoscope image data; and the second processor is further configured to transmit the ultrasonic image data and/or the laryngoscope image data to the first processor, so as to display an ultrasonic image and/or a laryngoscope image through a human-machine interaction component, and/or transmit the ultrasonic image data and/or the laryngoscope image data to a target device through a communication component.

In some embodiments, the defibrillation device further includes an extension function component which is connected with the second processor; wherein the extension function component includes at least one of: a data reading component, an extension human-machine interaction component, and a camera component.

In some embodiments, when the second processor is in a working state, the second processor is further configured to acquire the extension device data through at least one of the data reading component, the extension human-machine interaction component and the camera component, and to transmit the extension device data to a target device and/or the first processor.

In some embodiments, when the second processor is in a working state, the second processor is further configured to acquire feedback information for the extension device data, wherein the feedback information is transmitted by a target device.

In some embodiments, the defibrillation device further includes an extension monitoring component; wherein when the second processor is in a working state, the second processor is further configured to acquire data from the extension monitoring component and process said data.

In some embodiments, the defibrillation device further includes a power supply device; wherein a power supply terminal of the power supply device is connected with a power receiving terminal of the first processor and a power receiving terminal of the second processor, wherein an isolation circuit is provided between the power receiving terminal of the first processor and the power receiving terminal of the second processor.

In some embodiments, when a first preset condition occurs, the isolation circuit is configured to disconnect power supply to the second processor and meanwhile maintain power supply to the first processor.

In some embodiments, the defibrillation device further includes a power supply device; wherein the power supply device includes a first power supply terminal and a second power supply terminal, wherein the first power supply terminal is connected with a power receiving terminal of the first processor, and the second power supply terminal is connected with a power receiving terminal of the second processor.

In some embodiments, the power supply device further includes a switching component which is connected with the first power supply terminal and the second power supply terminal; wherein, when a first preset condition occurs, the switching component is configured to disconnect from the second power supply terminal and meanwhile maintain connection with the first power supply terminal.

In some embodiments, when a second preset condition occurs, the second processor is further configured to acquire data from the defibrillation component and/or a monitoring component and process said data to obtain the defibrillation data and/or monitoring data.

The defibrillation device provided in the embodiment of the present disclosure includes a defibrillation component, a first processor and a second processor. Wherein the defibrillation component is configured to perform a defibrillation task, the first processor is configured to acquire data from the defibrillation component and process said data to obtain defibrillation data; and the second processor is configured to acquire extension device data from an extension device, the second processor is connected with the first processor, and the second processor and the first processor are capable of transmitting preset information. In this defibrillation device, the defibrillation function is performed by the first processor, and the function of the extension device is performed by the second processor, such that the functional isolation between the defibrillation task and the extended task is achieved. The failure of the second processor or extension device does not affect the performance of the core defibrillation rescue function, so that the defibrillation device has high safety.

In a second aspect, an embodiment of the present disclosure provides a defibrillation device, including: a defibrillation component, which is configured to perform a defibrillation task; at least two processors, which at least include a first processor and a second processor; wherein, in a first state, the first processor is at least configured to acquire data from the defibrillation component and process said data to obtain defibrillation data, and at least configured to generate at least one piece of basic display information based on the defibrillation data, the second processor is at least configured to acquire data from at least one first extension device and process said data to obtain first extension device data, and configured to generate at least one piece of first extension display information based on the first extension device data; at least one processor of the at least two processors, includes a display fusion module: wherein the display fusion module is configured to, in the first state, receive the at least one piece of basic display information which is generated by the first processor and the at least one piece of first extension display information which is generated by the second processor, and to fuse the at least one piece of basic display information and the at least one piece of first extension display information to generate terminal display information; and a display which is configured to output the terminal display information.

In some embodiments, the first processor is configured to generate one piece of the basic display information, and/or the second processor is configured to generate one piece of the first extension display information.

In some embodiments, the first processor is configured to generate two pieces of the basic display information, and/or the second processor is configured to generate two pieces of the first extension display information.

In some embodiments, the defibrillation device further includes a monitoring component which is configured to perform a monitoring task; the first processor is further configured to acquire data from the monitoring component and process said data to obtain monitoring data, and configured to at least generate the at least one piece of basic display information based on the defibrillation data and the monitoring data.

In some embodiments, in order to at least generate the at least one piece of basic display information based on the defibrillation data and the monitoring data: the first processor is further configured to generate defibrillation display information based on the defibrillation data, and generate monitoring display information based on the monitoring data; and the display fusion module is further configured to receive the defibrillation display information and the monitoring display information which are generated by the first processor, and fuse the defibrillation display information and the monitoring display information to generate the basic display information.

In some embodiments, the first processor is further configured to acquire second extension device data from at least one second extension device and generate at least one piece of second extension display information based on the second extension device data; the display fusion module is further configured to receive the at least one piece of second extension display information which is generated by the first processor, and fuse the at least one piece of basic display information, the at least one piece of first extension display information and the at least one piece of second extension display information to generate the terminal display information.

In some embodiments, the second extension device includes a monitoring device; the first extension device includes at least one of: an ultrasound device, an endoscope device, a camera device, a ventilator, a compression machine, and an infusion pump.

In some embodiments, the first processor includes the display fusion module; the first processor is further configured to transmit the terminal display information to the display. In some embodiments, the second processor includes the display fusion module; the second processor is further configured to transmit the terminal display information to the display. In some embodiments, the at least two processors further include a third processor, wherein the third processor includes the display fusion module; the third processor is configured to transmit the terminal display information to the display.

In some embodiments, the first processor is further configured to control the defibrillation component to perform the defibrillation task.

In some embodiments, in a second state, the first processor is further configured to acquire data from the defibrillation component and process said data to obtain the defibrillation data, but not generate the basic display information.

In some embodiments, in a third state, the second processor is further configured to acquire data from the first extension device and process said data to obtain the first extension device data, but not generate the first extension display information.

In some embodiments, in order to fuse the at least one piece of basic display information and the at least one piece of first extension display information to generate terminal display information: the display fusion module is configured to superimpose the at least one piece of basic display information and the at least one piece of first extension display information to generate the terminal display information; or the display fusion module is further configured to join the at least one piece of basic display information and the at least one piece of first extension display information to generate the terminal display information.

In some embodiments, in order to fuse the at least one piece of basic display information, the at least one piece of first extension display information and the at least one piece of second extension display information to generate the terminal display information: the display fusion module is further configured to superimpose the at least one piece of basic display information, the at least one piece of first extension display information and the at least one piece of second extension display information to generate the terminal display information; or the display fusion module is further configured to join the at least one piece of basic display information, the at least one piece of first extension display information and the at least one piece of second extension display information to generate the terminal display information.

In some embodiments, the defibrillation device further includes a communication module, which is configured to establish a communication connection with the first extension device and/or a second extension device to acquire data from the first extension device and/or the second extension device through the communication connection, wherein the communication connection includes a wired connection, a wireless connection, or a plug-in connection.

In some embodiments, in a fourth state, the display fusion module is further configured to fuse the at least one piece of basic display information and abnormal display information to generate the terminal display information, wherein the abnormal display information is configured to indicate that the at least one piece of first extension display information and/or at least one piece of second extension display information are/is abnormal.

In some embodiments, the terminal display information includes a basic display area which corresponds to the basic display information and an extension display area which corresponds to the extension display information: wherein in the fourth state, the extension display area is configured to display the abnormal display information.

In a third aspect, an embodiment of the present disclosure provides a medical device, including: a basic component, which is configured to perform a basic medical function; at least one processor, which is at least configured to, in a first state, acquire data from the basic component, process said data to obtain basic data, and at least generate at least one piece of basic display information based on the basic data, and to acquire data from at least one first extension device, process said data to obtain first extension device data, and generate at least one piece of first extension display information based on the first extension device data: the at least one processor includes a display fusion module; wherein the display fusion module is configured to, in the first state, fuse the at least one piece of basic display information and at least one piece of extension display information to generate terminal display information, wherein the at least one piece of extension display information includes the at least one piece of first extension display information; the display fusion module is further configured to, in a fourth state, fuse the at least one piece of basic display information and abnormal display information to generate the terminal display information, wherein the abnormal display information is configured to indicate that the at least one piece of first extension display information is abnormal; and a display, which is configured to output the terminal display information.

In some embodiments, the at least one processor includes a first processor; wherein the first processor is at least configured to acquire data from the basic component, process said data to obtain basic data, and at least generate the at least one piece of basic display information based on the basic data, and to acquire data from the at least one first extension device, process said data to obtain the first extension device data, and generate the at least one piece of first extension display information based on the first extension device data.

In some embodiments, the first processor includes the display fusion module, and the first processor is further configured to transmit the terminal display information to the display.

In some embodiments, the at least one processor further includes a third processor, wherein the third processor includes the display fusion module: the third processor is configured to transmit the terminal display information to the display.

In some embodiments, the medical device includes a defibrillation device, and the basic component includes a defibrillation component of the defibrillation device which is configured to perform a defibrillation task; and the basic data includes defibrillation data.

In some embodiments, the defibrillation device further includes a monitoring component which is configured to perform a monitoring task; the first processor is further configured to acquire data from the monitoring component, process said data to obtain monitoring data, and at least generate the at least one piece of basic display information based on the defibrillation data and the monitoring data.

In some embodiments, in order to at least generate the at least one piece of basic display information based on the defibrillation data and the monitoring data: the first processor is further configured to generate defibrillation display information based on the defibrillation data, and generate monitoring display information based on the monitoring data; and the display fusion module is further configured to receive the defibrillation display information and the monitoring display information which are generated by the first processor, and fuse the defibrillation display information and monitoring display information to generate the basic display information.

In some embodiments, the first extension device includes at least one of: a monitoring device, an ultrasound device, an endoscope device, a camera device, a ventilator, a compression machine, and an infusion pump.

In some embodiments, the first processor is further configured to control the basic component to perform the basic medical function.

In some embodiments, the terminal display information includes a basic display area which corresponds to the basic display information and an extension display area which corresponds to the extension display information; wherein the extension display area is configured to, in the fourth state, display the abnormal display information.

In a fourth aspect, an embodiment of the present disclosure provides a display method for medical data, including: acquiring basic data, and at least generating at least one piece of basic display information based on the basic data; acquiring first extension device data, and generating at least one piece of first extension display information based on the first extension device data; in a first state, fusing the at least one piece of basic display information and at least one piece of extension display information to generate terminal display information, wherein the at least one piece of extension display information includes the at least one piece of first extension display information; and outputting the terminal display information.

In some embodiments, the method further includes: acquiring data from a basic component of a medical device and processing said data to obtain the basic data; and acquiring data from at least one first extension device and processing said data to obtain the first extension device data.

In some embodiments, the basic data includes defibrillation data of a defibrillation device, and the method further includes: acquiring monitoring data and generating the at least one piece of basic display information based on the defibrillation data and the monitoring data.

In some embodiments, generating the at least one piece of basic display information based on the defibrillation data and the monitoring data, includes: generating defibrillation display information based on the defibrillation data, and generating monitoring display information based on the monitoring data; fusing the defibrillation display information and the monitoring display information to generate the basic display information.

In some embodiments, the method further includes: in a fourth state, fusing the at least one piece of basic display information and abnormal display information to generate the terminal display information, wherein the abnormal display information is configured to indicate that the at least one piece of first extension display information is abnormal.

The defibrillation device, medical device and display method for medical data in embodiments of this disclosure use a display fusion method to generate the terminal display information, such that the basic display information and extension display information never mutually affect each other and better risk isolation effect is achieved. When connecting a new extension device, just the new extension display information is generated and then fused with the original display information, without modifying the original display information, which makes the scalability more flexible.

It should be understood that the above general description and the detailed description below are only illustrative and explanatory, and do not limit the disclosure of embodiments of this disclosure.

BRIEF DESCRIPTION OF THE DRAWINGS

In order to explain embodiments of this disclosure more clearly, the following will briefly introduce drawings required in the description for the embodiments. It is obvious that the drawings in the following description are only some embodiments of this disclosure. For those skilled in the art, other drawings can be obtained from these accompanying drawings without paying any creative works.

10

Figures 11A, 11B:
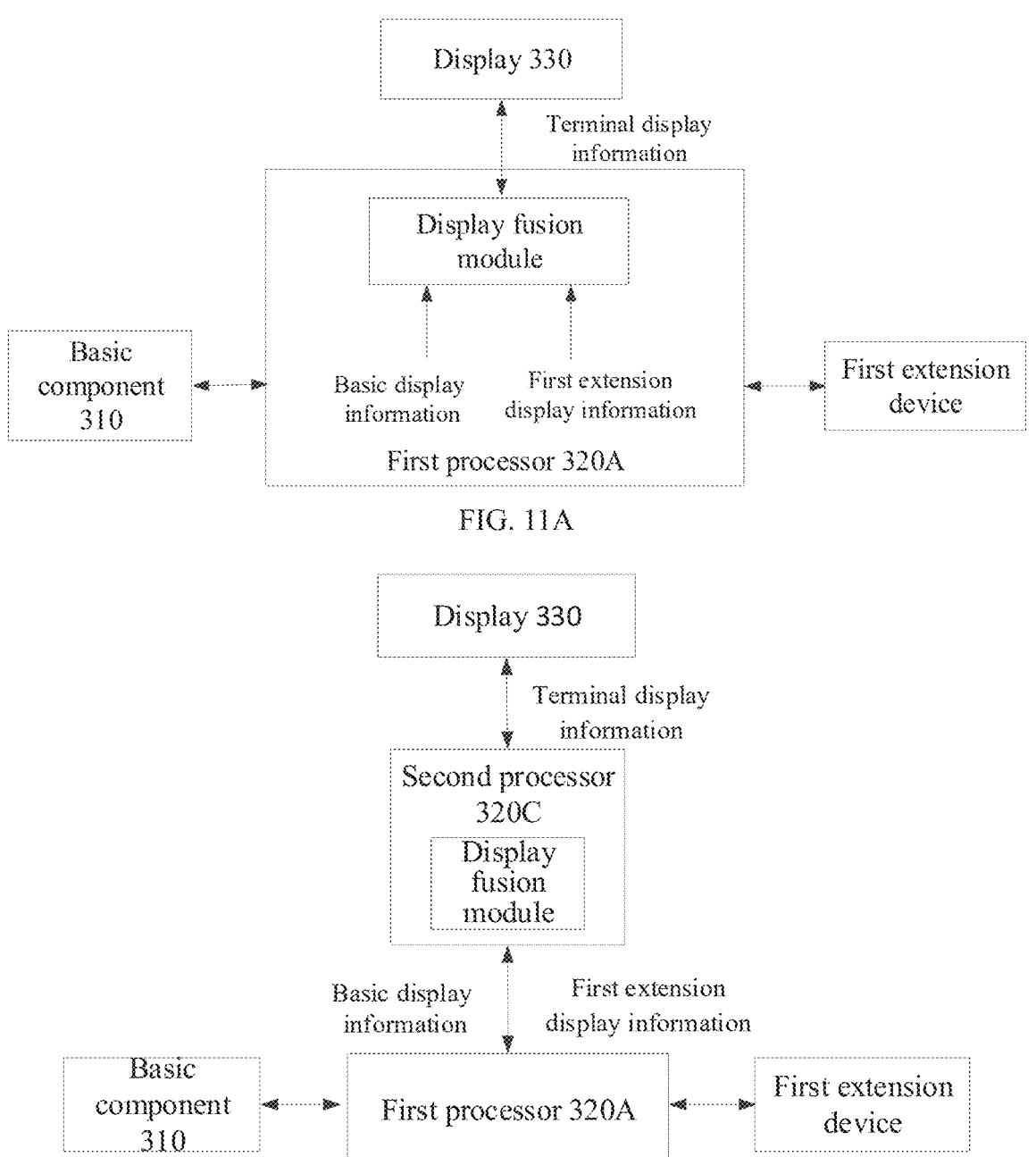

FIGS. 11A-11B illustrate a structural block diagram of a medical device according to some embodiments of this disclosure.

FIG. 12 illustrates a schematic flowchart of a display method for medical data according to an embodiment of this disclosure.

Figure 13:
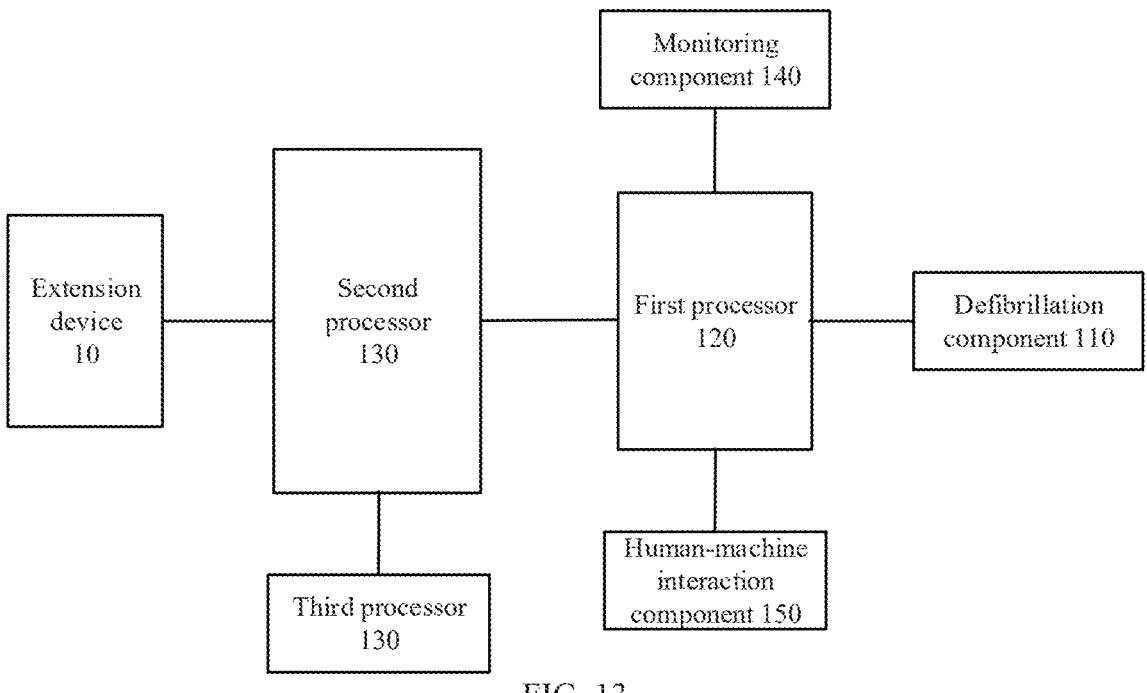

FIG. 13 is a structural diagram of defibrillation device in a further different embodiment.

DETAILED DESCRIPTION

The technical solutions in example embodiments of the disclosure will be described clearly and completely below with reference to the accompanying drawings. Apparently, the embodiments described are merely some, rather than all, of the embodiments of the disclosure. It should be understood that the disclosure is not limited by the example embodiments described herein. All other embodiments derived by those skilled in the art without creative efforts on the basis of the embodiments described in the disclosure shall fall within the protection scope of the disclosure.

The flowchart shown in the attached drawings is only an example, and it is not necessary to include all the content and operations/steps, nor must be executed in the described order. For example, some operations/steps can also be decomposed, combined, or partially merged, so that the actual order of execution may vary depending on the actual situation.

Some embodiments of this disclosure are described in detail below in conjunction with the accompanying drawings. Without conflict, the following embodiments and the features in the embodiments can be combined with each other.

The terms used herein are intended only to describe specific embodiments and are not intended as a limitation of this disclosure. When used herein, the singular forms of "a", "one", and "the/said" are also intended to include the plural form, unless the context clearly indicates otherwise. It should also be understood that the terms "constitute" and/or "include", "comprise", when used in this disclosure, determine the presence of said features, integers, steps, operations, elements, and/or components, but do not exclude the presence or addition of one or more other features, integers, steps, operations, elements, components, and/or groups. When used herein, the term "and/or" includes any and all combinations of relatively listed items.

For a thorough understanding of the present disclosure, a detailed structure is proposed in the following description to explain the technical solution proposed by the present disclosure. The optional embodiments of the present disclosure are described in detail below, but in addition to these detailed descriptions, the present disclosure may have other embodiments.

Figures 1, 2:
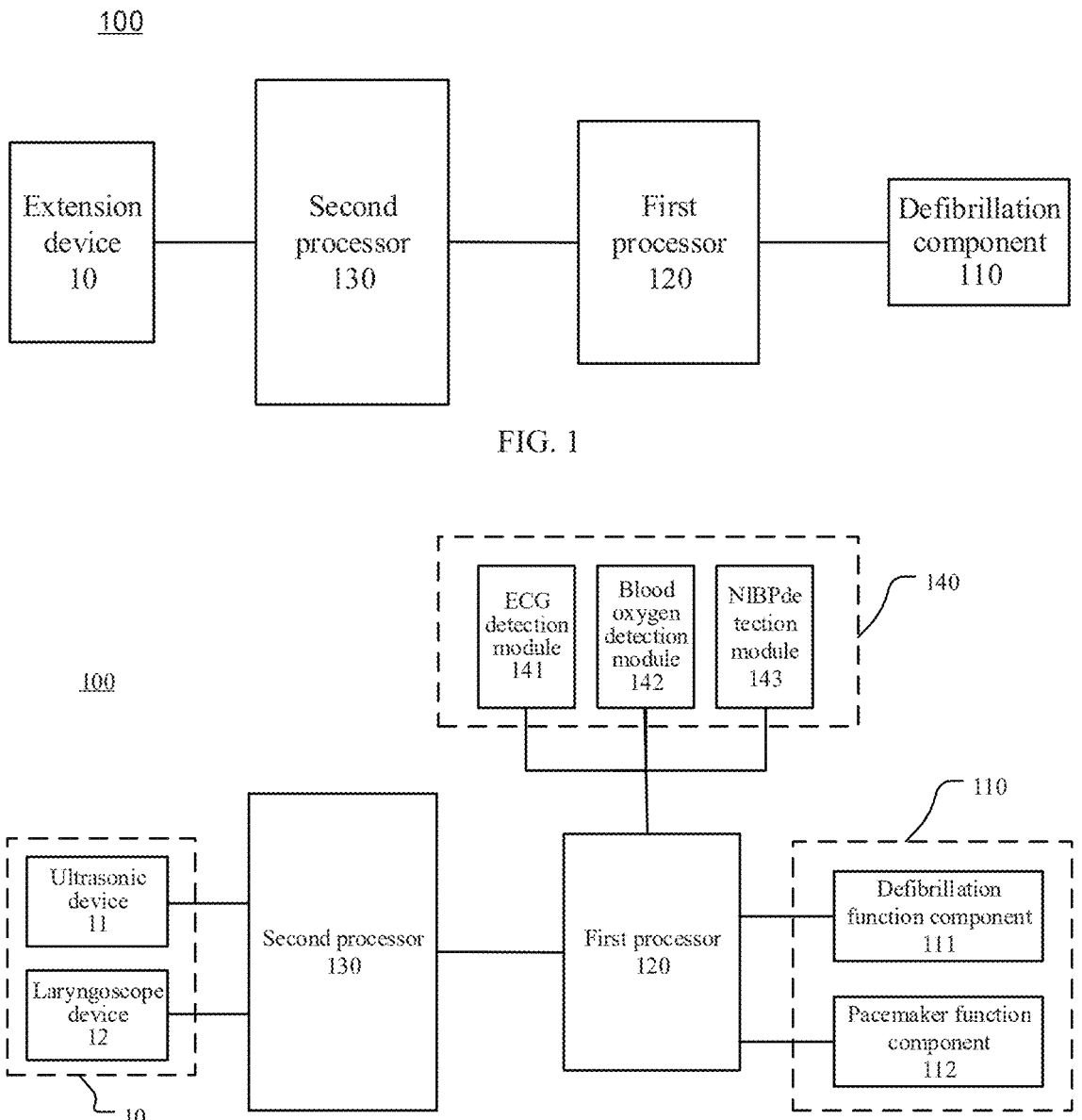
FIG. 1 is a structural diagram of a defibrillation device provided in an embodiment of this disclosure.
FIGS. 2 to 8 are structural diagrams of defibrillation devices in different embodiments.

Please refer to FIG. 1, which is a schematic block diagram of a defibrillation device 100 provided in an embodiment of this disclosure. Defibrillation device 100 is a high-risk first aid device mainly used for defibrillation treatment of dangerous diseases, such as cardiac ventricular fibrillation and atrial fibrillation. Optionally, the defibrillation device 100 includes at least one of the following: an ambulance defibrillator, an emergency hospital defibrillator, and an automatic external defibrillator (AED), but is not limited thereto.

As shown in FIG. 1, the defibrillation device 100 includes a defibrillation component 110, a first processor 120, and a second processor 130. The defibrillation component 110 is configured to perform a defibrillation task.

Exemplarily, the defibrillation component 110 includes a charge and discharge circuit which is configured to boost and store low-voltage DC electrical energy in an energy storage capacitor, and release the stored electrical energy from the energy storage capacitor to output a defibrillation waveform.

For example, the defibrillation component 110 is connected or can be connected with a defibrillation electrode, and the charge and discharge circuit performs a discharge treatment to a body of a patient through the defibrillation electrode according to an instruction of the first processor 120. For example, when performing a defibrillation task, the defibrillation component 110 at least controls the charge and discharge circuit to release the electrical energy stored by the energy storage capacitor and output a defibrillation waveform.

In some embodiments, refer to FIG. 2. The defibrillation device 100 also includes a monitoring component 140, and the first processor 120 also acquires data from the monitoring component 140 and processes the same to obtain monitoring data.

Exemplarily, the monitoring component 140 is configured to acquire monitoring data, such as a physiological data signal from the patient, which includes such as at least one of the following: an electrocardiogram (ECG) signal, blood oxygen saturation, automated noninvasive blood pressure (NIBP), arterial blood pressure, body temperature, heart rate, respiratory impedance, and of course, it is not limited to this.

Exemplarily, the monitoring component 140 includes at least one of the following: an ECG detection component 141, a blood oxygen detection component 142, and an NIBP detection component 143. For example, the monitoring component 140 is connected or can be connected with an electrode slice, such as a disposable ECG electrode slice. The ECG detection component 141 acquires an ECG signal through the electrode slice which is attached to the body of the patient, and processes the ECG signal to obtain at least one of following: heart rate, PR interval, QRS interval, and the likes. The monitoring component 140 is connected or can be connected with a blood oxygen probe, and the blood oxygen detection component 142 can determine the blood oxygen saturation of the patient according to signals which are output from the blood oxygen probe. Of course, it is not limited to this. For example, the monitoring component 140 can transmit the digital signal which is output by the blood oxygen probe and indicates the blood oxygen saturation to the first processor 120.

In some embodiments, the first processor 120 is configured to acquire monitoring data through the monitoring component 140 and perform the defibrillation task through the defibrillation component 110.

Exemplarily, the first processor 120 is configured to control the defibrillation component 110 to perform a defibrillation task according to the monitoring data. For example, the defibrillation task includes, but is not limited to, biphasic wave defibrillation. For example, when an electrocardiogram electrode slice is contacted with a suitable body part of the patient, the monitoring component 140 acquires and analyzes treatment related information. For example, the monitoring component 140 measures impedance information of the contact circuit between the electrode slice and the human body, determines, through detecting the human body impedance, whether the electrode slice and the human body are in good contact and whether the patient has a movement, serves this information as a reference for subsequent biphasic wave shock defibrillation adjustment parameter meanwhile, detects whether the patient has an internal pacemaker and acquires an Pace tag of the pacemaker when it is detected, and acquires, through the electrocardiogram electrode slice, ECG (electrocardiogram) waveform data of the human body.

The first processor 120 synthesizes the above analysis results of contact impedance, Pace signal, and ECG waveform data to determine whether the patient is ready and whether a defibrillation rhythm is detected. If the defibrillation rhythm is detected, the defibrillation component 110 is started to treat the patient.

Exemplarily, the defibrillation component 110 includes a defibrillation function component 111 and/or a pacemaker function component 112. Among them, the defibrillation function module 111 is mainly aimed at malignant arrhythmia, such as pulseless ventricular tachycardia and ventricular fibrillation. Through defibrillation, arrhythmia that may endanger life can be treated to save the lives of patients and effectively prevent sudden death. Pacemaker function component 112 is mainly aimed at patients with slow heart rate, such as patients with problems of cardiac conduction system, no mater patients with problem of sinus node function, cardiac pacing, or atrioventricular node, it can stimulate the heart to initiate an effective cardiac pacing. Regarding the patients with problem of atrioventricular node, pacemaker function component 112 can also replace the atrioventricular node for conduction. Understandably, the defibrillation function component 111 mainly performs termination treatment for arrhythmia, while the pacemaker function component 112 is mainly for patients with slower heart rhythm to maintain the heart rate within a normal range.

The first processor 120 acquires data from the defibrillation component 110 and processes the data to obtain defibrillation data. For example, the first processor 120 acquires at least one of the defibrillation energy, the number of shocks, and the likes from the defibrillation component 110 and processes the same to obtain defibrillation data, which is not limited to this.

In some embodiments, referring to FIG. 2, the extension device 10 includes an ultrasonic device 11 and/or a laryngoscope device 12. Wherein the ultrasonic device 11 can transmit ultrasonic waves to a target object, receive ultrasonic echoes of the ultrasonic waves returned by the target object, obtain an ultrasonic echo signal, and generate an ultrasonic image based on the ultrasonic echo signal. Alternatively, the ultrasonic device 11 can receive the ultrasonic echo signal through transmitting ultrasonic waves to the target object and receiving the ultrasonic echoes of the ultrasonic waves which are returned by the target object. Understandably, the ultrasonic device 11 may include a complete ultrasound imaging device, or may only include an acquiring device for ultrasound echo signal, such as an ultrasound probe.

Among them, the laryngoscope device 12, for example, is an electronic laryngoscope, which includes a camera, and also includes a light source. The scope of an electronic laryngoscope inspection includes a nasal cavity, nasopharynx, oropharynx, hypopharynx, and larynx, and can even go deep into an positive airway to understand the situation of trachea, thus providing a clearer basis for inner and lower limits of pathological range of laryngeal tumors.

Specifically, the second processor 130 acquires extension device data from the extension device 10. Exemplarily, the second processor 130 acquires extension device data from the extension device 10, includes followings. The second processor 130 acquires ultrasonic data and/or laryngoscope data from the ultrasonic device 11 and/or the laryngoscope device 12. For example, the ultrasonic data is ultrasound image data, such as an ultrasound image which is generated by ultrasonic device 11, and/or the laryngoscope data is laryngoscope image data. Of course, it is not limited to this, for example, the ultrasonic data is the ultrasonic echo signal which is acquired by the ultrasonic device 11.

As an example, the second processor 130 can process the acquired extension device data. For example, the second processor 130 acquires the ultrasound echo signal acquired by the ultrasonic device 11 and generates an ultrasound image based on the ultrasound echo signal. Specifically, in the defibrillation device 100, the defibrillation function and monitoring function can be realized through the first processor 120, and the extension function of the extension device 10 can be realized through the second processor 130 to achieve functional isolation between the defibrillation function, monitoring function, and extension function. The failure of the second processor 130 or the failure of the extension device 10 does not affect the first processor 120 to acquire and process data from the defibrillation component 110 to obtain the defibrillation data, does not affect the performance of the core defibrillation rescue function. In this way, the defibrillation device 100 has a high safety.

It is understandable that the defibrillation device 100 of the embodiment of this disclosure adopts a multiprocessor architecture. The first processor 120 can serve as the main processor and be mainly responsible for routine defibrillation monitoring functions and tasks, which for example include: a defibrillation function, pacing function, ECG acquisition and algorithm analysis, key or touch screen input, and other functions. Another second processor 130 can serve as an extension processor to take charge of some external extension functions, such as ultrasound, camera, etc., and these external extension functions can be continuously extended according to clinical needs. It can be determined that the defibrillation device 100 has strong scalability. In comparison, the processor of traditional defibrillation device is difficult to quickly update due to safety and stability requirements, resulting in limited performance. If new applications or functions are to be added on the basis of the monitoring and defibrillation functions, the expanded functions cannot be too complex. However, the expanded processing system in the embodiment of this disclosure is basically not limited to the stability requirements of the defibrillation device because it does not have to perform defibrillation functions, so new processors with higher performance can be adopted, and the defibrillation device 100 can be updated and expanded at any time, making its performance improvement easier.

It should be noted that defibrillation devices are emergency devices and need extremely high safety requirements. Traditional defibrillation processors can meet requirements when handling defibrillation monitoring tasks. However, if complex functions are continuously extended and expanded, the single processor has extremely high risk, and its performance may not satisfy the complex task system and complex software management. Accordingly, the risk of the product is greatly increased. The defibrillation device 100 in the embodiment of this disclosure uses a multiprocessor architecture, with a first processor 120 specifically responsible for defibrillation and monitoring functions, and a second processor 130 responsible for extended complex functions that require a large amount of data processing. Such a multiprocessor architecture can effectively solve such problems mentioned above.

Specifically, refer to FIGS. 1 and 2. The second processor 130 is connected with the first processor 120, and the second processor 130 and the first processor 120 are capable of transmitting preset information.

It is understandable that, there is data and/or instruction transmission between the first processor 120 and the second processor 130 of the defibrillation device 100 to achieve harmony and coordination between the defibrillation functions, monitoring functions, and extension functions, namely, a multifunctional integrated defibrillation device 100.

In some embodiments, the second processor 130 transmits preset information unidirectionally to the first processor 120, while in other embodiments, preset information may be transmitted bidirectionally between the first processor 120 and the second processor 130.

In some embodiments, the second processor 130 transmits acquired extension device data, such as ultrasound image data and/or laryngoscope image data, to the first processor 120.

In some embodiments, the second processor 130 processes the acquired extension device data and transmits it to the first processor 120.

Exemplarily, the second processor 130 is further configured to process ultrasonic data and/or laryngoscope data to generate ultrasound image data and/or laryngoscope image data. For example, when the extension device 10 mainly includes a separate acquisition device, processing is required to obtain the image data. For example, the second processor 130 processes the ultrasound echo signal acquired from the ultrasonic device 11 to generate the ultrasound image data based on the ultrasound echo signal, and transmits the ultrasound image data to the first processor 120.

Exemplarily, the first processor 120 obtains defibrillation data through the defibrillation component 110 according to the extension device data, and/or obtains monitoring data through the monitoring component 140, and/or performs a defibrillation task through the defibrillation component 110.

For example, the extension device data can be configured to indicate a situation of the patient. For example, when the extension device data indicates that the situation of the patient is suitable for defibrillation, the defibrillation component 110 performs the defibrillation task.

For example, the extension device data can be configured to indicate the state of medical personnel, that is, the state of user. For example, when the extension device data indicates that medical personnel are performing ultrasound diagnosis on the patient, the first processor 120 automatically starts acquiring monitoring data through the monitoring component 140 according to the extension device data, and can also perform the defibrillation task through the defibrillation component 110 after the ultrasound diagnosis is completed.

Figure 3:
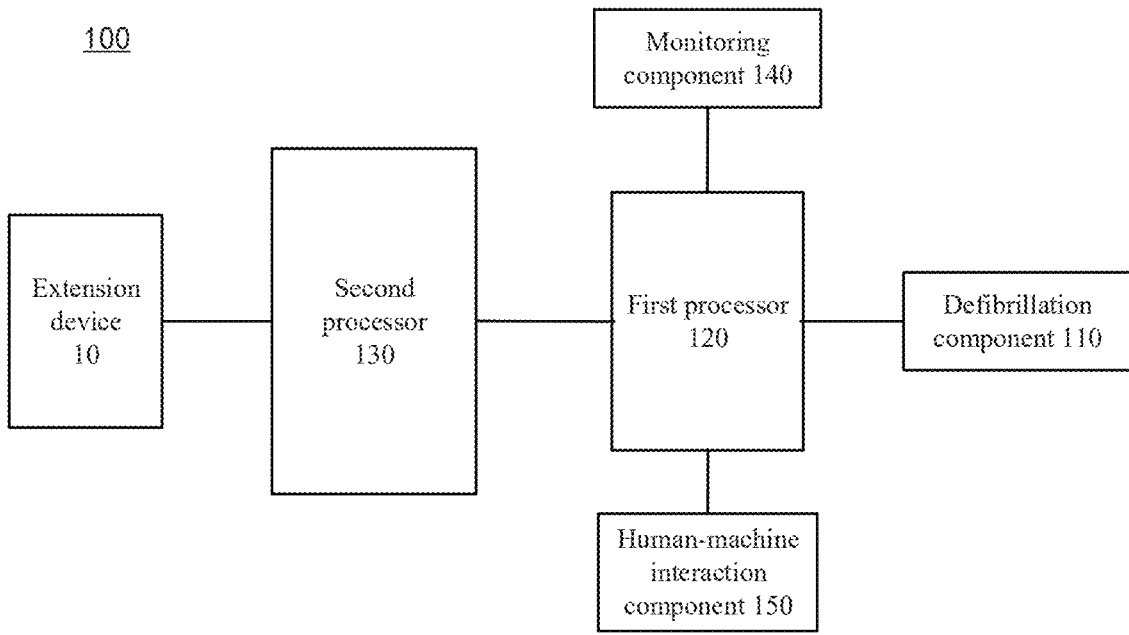
Figure 4:
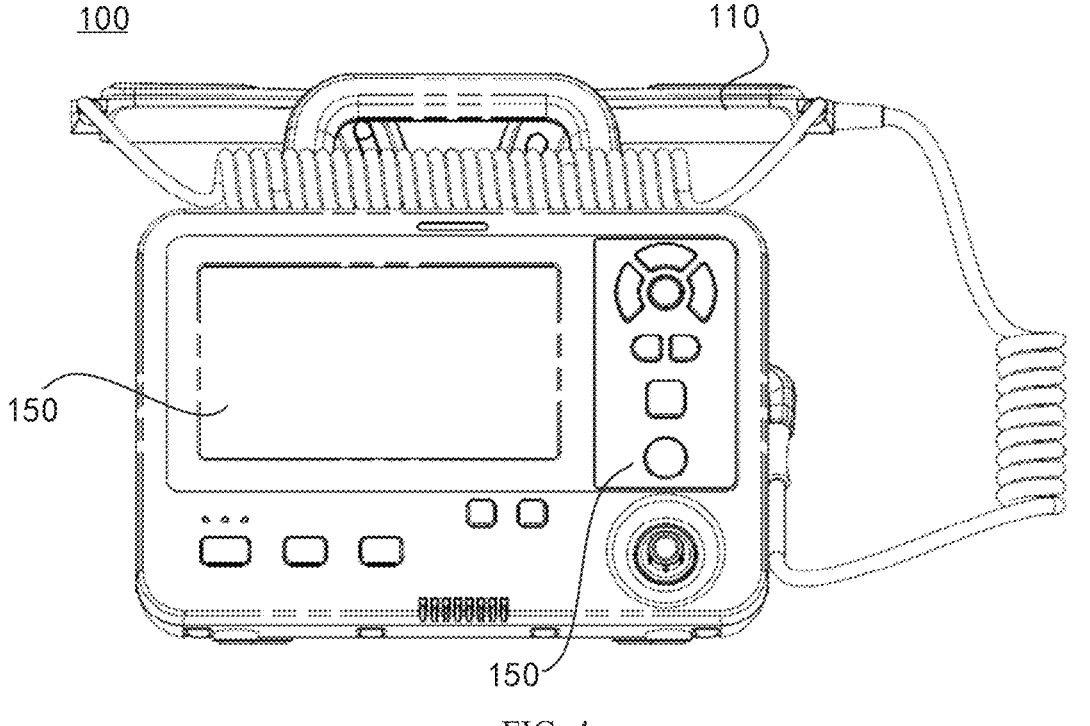

In some embodiments, as shown in FIGS. 3 and 4, the defibrillation device 100 also includes a human-machine interaction component 150. Optionally, the human-machine interaction component 150 is connected with the first processor 120. Of course, it is not limited to this. For example, the human-machine interaction component 150 can also be connected with the second processor 130. When the second processor 130 is in a low-power or working state, it can acquire instructions through the human-machine interaction component 150.

Exemplarily, the human-machine interaction component 150 includes, for example, at least one of the following: a display component, a mouse, a keyboard, a touch pad, a touch display component, a key, a knob, a microphone, a speaker, and an alert light. It should be noted that some human-machine interaction components 150, such as a mouse, can be detachably connected with the main body of the defibrillation device 100.

For example, the second processor 130 is further configured to transmit ultrasound image data and/or laryngoscope image data to the first processor 120 to display ultrasound images and/or laryngoscope images through the human-machine interaction component 150.

As an example, the first processor 120 outputs the defibrillation data and/or the monitoring data and/or the data transmitted by the second processor 130 through the human-machine interaction component 150.

In some embodiments, the first processor 120 displays the defibrillation data and/or the monitoring data through a display interface of the human-machine interaction component 150, and superimposes the data transmitted by the second processor 130 on a partial display area of the display interface when outputting the data transmitted by the second processor 130 through the human-machine interaction component. By superimposing and displaying the data transmitted by the second processor 130, such as ultrasound images and/or laryngoscope images, on the partial display area of the display interface which displays the defibrillation data and/or the monitoring data, it is not necessary to perform data fusion processing on the ultrasound image and/or the laryngoscope image with the defibrillation data and/or the monitoring data, and the ultrasound image and/or the laryngoscope image can be directly displayed with high real-time performance and good security, which can prevent delays and jams in the image display. Displaying the data transmitted by the second processor 130 in a windowed or picture-in-picture manner allows users to further analyze the situation of the patient according to the data transmitted by the second processor 130 when viewing defibrillation data and/or the monitoring data.

In other embodiments, the first processor 120 generates target visual information according to the defibrillation data and/or the monitoring data and/or the data transmitted by the second processor 130. The human-machine interaction component 150 is configured to output the target visual information.

It should be noted that the target visual information is used for display on the same display interface. For example, the first processor 120 fuses the defibrillation data and/or the monitoring data, as well as data which is transmitted by the second processor 130, to obtain the image data to be displayed. The fusion can be hardware fusion or software fusion. For example, the first processor 120 is configured to generate a target image according to the monitoring data and the extension device data which is transmitted by the second processor 130, and output the target image through the human-machine interaction component 150. Optionally, the different regions of the target image are respectively regions of the defibrillation data, the monitoring data, and the extension device data. Optionally, the target image is obtained by superimposing the extension device data onto the image of defibrillation data or monitoring data. Of course, it is not limited to this. For example, the first processor 120 can display the defibrillation data, the monitoring data, and the extension device data in a time-sharing manner through a display component.

For example, the second processor 130 transmits the extension device data, such as ultrasound image data, to the first processor 120, which displays the extension device data together with the monitoring data and/or the defibrillation data through the human-machine interaction component 150. When the second processor 130 fails or the extension device 10 fails, it does not affect the first processor 120 to display the information, such as the defibrillation data and the monitoring data, such that the whole device has high security.

In some embodiments, when the human-machine interaction component 150 is connected with the first processor 120, the human-machine interaction component 150 can perform at least some human-machine interaction functions corresponding to the defibrillation function and the monitoring function. It is also possible for the human-machine interaction component 150 to implement at least some of the human-machine interaction functions of the extension device 10 for facilitating user operation. Of course, it is not limited to this. For example, the human-machine interaction functions of the extension device 10, corresponding to the defibrillation function and the monitoring function, can also be implemented based on different human-machine interaction components 150.

Exemplarily, the first processor 120 is configured to acquire an operation instruction through the human-machine interaction component 150. For example, the first processor 120 is configured to acquire an operation instruction for the extension device 10, and transmit the operation instruction for the extension device 10 to the second processor 130. The second processor 130 is configured to control the extension device 10 to perform a corresponding extension task according to the operation instruction. The extension device 10 in this example can be a complete device, such as a complete ultrasonic device, capable of generating ultrasound images based on the ultrasound echo signals acquired by the acquisition device.

For example, the first processor 120 is configured to determine whether the operation instruction, which is acquired through the human-machine interaction component 150, is the operation instruction for the extension device 10, and to transmit the operation instruction for the extension device 10 to the second processor 130. Of course, it is not limited to this. For example, the first processor 120 can transmit all the operation instructions acquired through the human-machine interaction component 150 to the second processor 130, which determines whether the operation instructions are for the extension device 10.

Exemplarily, the display component in the human-machine interaction component 150 provides a first operation interface/region and a second operation interface/region. The first processor 120 can control the display component to display the first operation interface/region or the second operation interface/region according to an operation of the user to the human-machine interaction component 150. When the user inputs an operation instruction in the second operation interface/region, the obtained operation instruction is transmitted to the second processor 130. When the user inputs an operation instruction in the first operation interface/region, it is determined that the operation instruction is not an operation instruction for the extension device 10.

Exemplarily, the display component can be configured to display the first display interface/area and the second display interface/area. Optionally, the first display interface/area can be configured to display the monitoring data and/or the defibrillation data, and the second display interface/area can be configured to display the extension device data, such as ultrasound image data. When the first processor 120 detects an operation in the second region, it can transmit the acquired operation instruction to the second processor 130.

Exemplarily, the operation instruction for the extension device 10 is configured to indicate that the extension device 10 is in an on-state or an off-state, such as, to indicate the second processor 130 to start acquiring ultrasound images through the ultrasonic device 11, to indicate the second processor 130 to adjust an imaging mode (such as continuous Doppler mode, pulsed Doppler mode) and imaging parameters (such as Doppler frequency) of the ultrasonic device 11, and of course, it is not limited thereto. For example, the operation instruction for the extension device 10 can also be configured to indicate to adjust a brightness of a light source on the laryngoscope device 12. When the second processor 130 fails or the extension device 10 fails, it does not affect the first processor 120 to acquire the operation instructions for the defibrillation function and the monitoring function through the human-machine interaction component 150, and according to the operation instructions, to acquire the defibrillation data through the defibrillation component 110 and/or the monitor data through the monitoring component 140 and/or to perform the defibrillation task through the defibrillation component 110.

Exemplarily, the first processor 120 is configured to acquire the operation instruction for the second processor 130 through the human-machine interaction component 150 and transmit the operation instruction to the second processor 130. The second processor 130 processes the acquired extension device data according to the operation instruction. Optionally, the extension device 10 in this example includes only an acquisition device, such as an ultrasound probe. The second processor 130 generates an ultrasound image based on the ultrasound echo signal acquired by the acquisition device according to the operation instruction.

Figure 5:
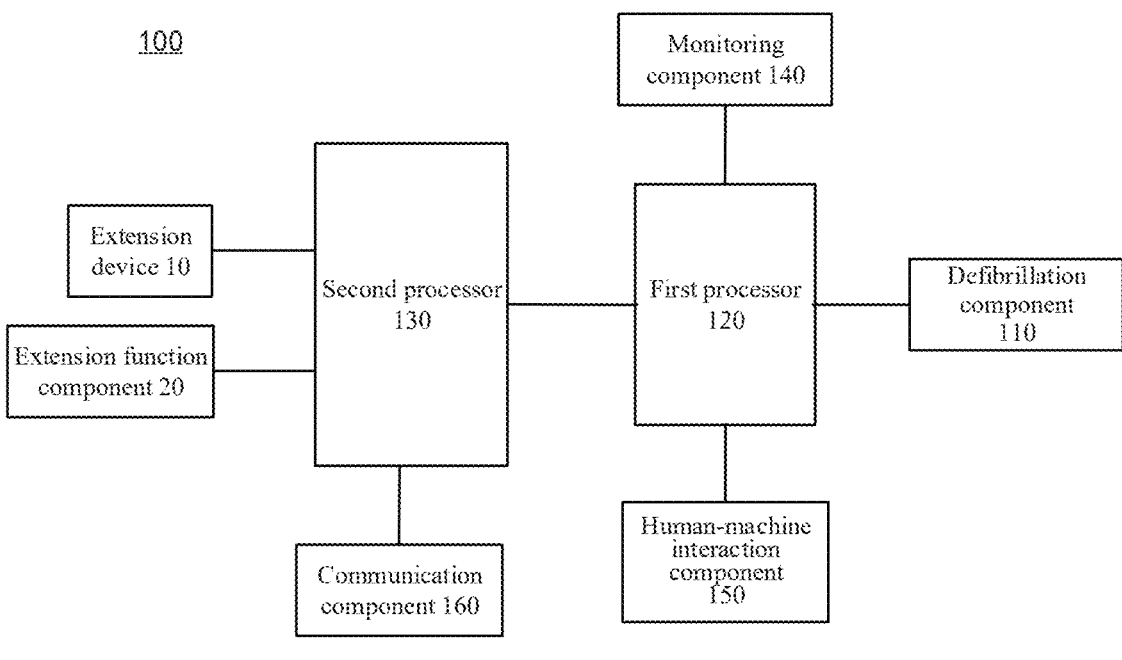

In some embodiments, referring to FIG. 5, the defibrillation device 100 further includes a communication component 160. As shown in FIG. 5, the communication component 160 is connected with the second processor 130. The communication component 160 can be configured to implement an external communication function of the defibrillation device 100.

Exemplarily, the communication component 160 can include at least one of the following: a video transmission interface, a network cable interface, an USB interface, and a wireless communication component 160. The video transmission interface includes, for example, a High Definition Multimedia Interface (HDMI), and the wireless communication component 160 includes, for example, a 5G (5th Generation Mobile Communication Technology) component. Of course, it is not limited to this, for example, a 4G (Fourth Generation Mobile Communication Technology) component can also be included. When the communication component 160 fails, it does not affect the first processor 120 to acquire data from the defibrillation component 110 and process the data to obtain defibrillation data, which has high security.

Exemplarily, the first processor 120 generates the target visual information according to the defibrillation data and/or the monitoring data and/or the data transmitted by the second processor 130, and transmits the generated target visual information to the second processor 130. And the second processor 130 transmits the target visual information to a target device through the communication component 160. For example, the target image displayed by the first processor 120 through the human-machine interaction component 150 is consistent with the target image displayed by the target device to better adapt to user habit.

Exemplarily, the first processor 120 is further configured to transmit the defibrillation data and/or the monitoring data to the second processor 130. The second processor 130 is configured to transmit the defibrillation data and/or the monitoring data to the target device through the communication component 160. For example, the target device includes, for example, at least one of a server and a terminal device, and user of the target device and/or the target device can provide remote guidance according to the monitoring data.

Exemplarily, the second processor 130 is further configured to transmit acquired or processed extension device data to the target device through the communication component 160. For example, the second processor 130 is further configured to transmit the ultrasound image data and/or the laryngoscope image data to the target device through the communication component 160. The target device and/or the user of the target device can provide remote guidance according to the extension device data, such as ultrasound image data.

Exemplarily, the first processor 120 is further configured to transmit the defibrillation data and/or the monitoring data to the second processor 130, and the second processor 130 is further configured to transmit the defibrillation data and/or the monitoring data, as well as the acquired or processed extension device data, to the target device through the communication component 160. For example, the second processor 130 is configured to generate the target visual information according to the defibrillation data and/or the monitoring data and the acquired or processed extension device data, and transmit the target visual information to the target device through the communication component 160.

In some embodiments, referring to FIG. 5, the defibrillation device 100 also includes an extension function component 20 which is connected with the second processor 130.

Exemplarily, the extension function component 20 includes at least one of the following: a data reading component, an extension human-machine interaction component, and a camera component.

The data reading component includes at least one of the following: a magnetic stripe card reading component, a chip card reading component, and a near field communication (NFC) component, but is not limited to this.

Exemplarily, the second processor 130 acquires the extension device data through at least one of the data reading component, the extension human-machine interaction component, and the camera component, and transmits the extension device data to the target device and/or the first processor 120.

Exemplarily, a user can input an operation instruction to acquire and transmit the extension device data through the extension human-machine interaction component, and the second processor 130 transmits the extension device data to the target device and/or the first processor 120 according to the operation instruction.

Exemplarily, the second processor 130 can read data which is stored by a preset device and/or an image which is photographed by the camera component through the data reading component. For example, the second processor 130 reads data from such as an ID card or social security card through the data reading component, or images of the patient or a body part of the patient body which are photographed by the camera component, or images of an emergency scene which are photographed by the camera component. Optionally, the data stored by the preset device, such as medical history, medication situation of the patient, and the likes, which is read by the second processor 130, can be used by the first processor 120 as a reference for performing defibrillation tasks.

Exemplarily, the second processor 130 may also transmit the data which is read by the data reading component and/or the images which are photographed by the camera component to the target device, and obtain feedback information transmitted by the target device according to the data and/or images. For example, the second processor 130 transmits the data which is read from the social security card to the server and obtains feedback information from the server. The feedback information includes, for example, at least one of the following: medical history and medication situation of the patient. For example, the second processor 130 transmits an image of a patient or a body part of the patient, or a scene image to a target device for remote guidance or arrangement of first aid from the user of the target device and/or from the target device.

Understandably, the second processor 130 is further configured to acquire the feedback information which is transmitted by the target device for the extension device data. Exemplarily, the target device can automatically determine and transmit the feedback information according to the extension device data, or can output the extension device data to a user, determine and transmit the feedback information according to an operation of the user.

For example, the second processor 130 is further configured to transmit the feedback information to the first processor 120, the first processor 120 outputs the feedback information through the human-machine interaction component 150 to guide the user of the defibrillation device 100 or to output information required by the user.

Figure 6:
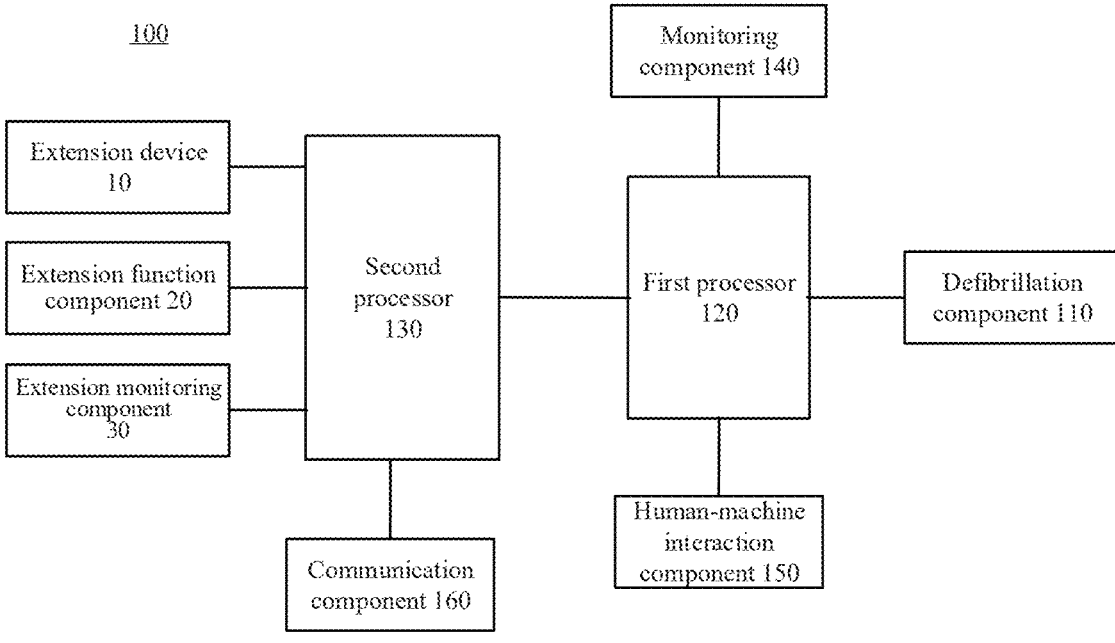

In some embodiments, refer to FIG. 6. The defibrillation device 100 also includes an extension monitoring component 30, and the second processor 130 also acquires data from the extension monitoring component 30 and processes the same.

Exemplarily, the extension monitoring component 30 can be configured to acquire monitoring data different from the aforementioned monitoring component 140, such as at least one of carbon dioxide ($CO_2$), body temperature, respiratory impedance, and the likes. Optionally, the extension monitoring component 30 includes a temperature sensor, and the likes. Of course, it is not limited to this. For example, the extension monitoring component 30 can acquire the same monitoring data as the aforementioned monitoring component 140.

As an example, the second processor 130 either transmits the data acquired from the extension monitoring component 30 or processes the data acquired from the extension monitoring component 30 and then transmits it to the first processor 120. The first processor 120 outputs the data through the human-machine interaction component 150, or the first processor 120 performs a defibrillation task through the defibrillation component 110 according to the data. The types of monitoring data can be flexibly extended by the extension monitoring component 30 according to the usage scenario, thus improving the accuracy of the first processor 120 when performing defibrillation through the defibrillation component 110.

Figures 7, 8:
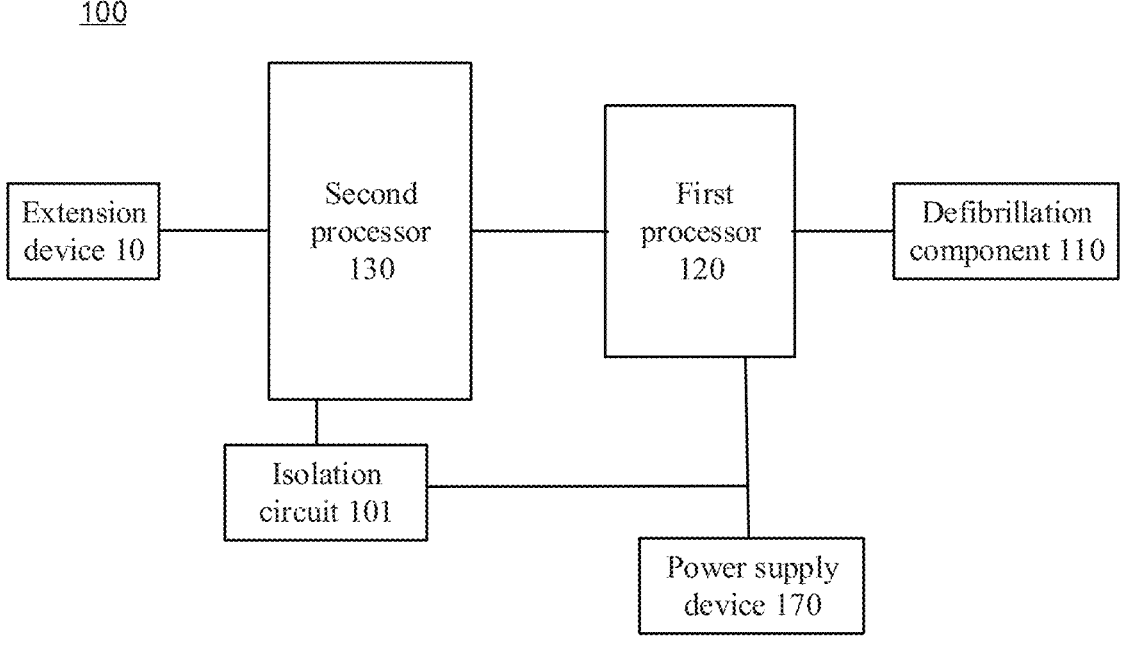

In some embodiments, refer to FIGS. 7 and 8, the defibrillation device 100 further includes a power supply device 170.

As shown in FIG. 7, for example, a power supply terminal of the power supply device 170 is connected with a power receiving terminal of the first processor 120 and a power receiving terminal of the second processor 130, and an isolation circuit 101 is provided between the power receiving terminal of the first processor 120 and the power receiving terminal of the second processor 130, which can prevent negative effects on the function of the first processor 120 in the event of the failure of the second processor 130, such as a short circuit.

As an example, the isolation circuit 101 is configured to, when a first preset condition occurs, disconnect the power supply to the second processor 130 and maintain the power supply to the first processor 120 meanwhile.

For example, the isolation circuit 101 is configured to disconnect the power supply to the second processor 130, when a failure of at least one of the second processor 130, the extension device 10, the extension function component 20, and the extension monitoring component 30, occurs. Alternatively, or additionally, the isolation circuit 101 is configured to disconnect the power supply to the second processor 130 when a supply power of the power supply device 170 is lower than a preset value. Therefore, it is possible to prevent the negative effects of the failures of the second processor 130, the extension device 10, the extension function component 20, and the extension monitoring component 30, such as a short circuit or an insufficient power supply, on the functions of the first processor 120, and prioritize the power demand for the defibrillation function, the monitoring function, and the human-machine interaction function.

Optionally, the isolation circuit 101 can also be configured to disconnect the power supply to the second processor 130 when a processor state of the second processor 130 needs to be switched to a turn-off state. This can reduce the power consumption of the defibrillation device and reduce the negative effect of the second processor 130, the extension device 10, the extension function component 20, and the extension monitoring component 30 on the functions of the first processor 120.

As shown in FIG. 8, the power supply device 170 includes a first power supply terminal and a second power supply terminal, wherein the first power supply terminal is connected with the power receiving terminal of the first processor 120, and the second power supply terminal is connected with the power receiving terminal of the second processor 130. By supplying power to the first processor 120 and the second processor 130 through different power supply terminals, it is possible to prevent the negative effect of the failure of the second processor 130, such as a short circuit, on the functionality of the first processor 120.

As shown in FIG. 8, the power supply device 170 further includes a switching component 102 that is connected with the first power supply terminal and the second power supply terminal. The switching component 102 disconnects from the second power supply terminal, while maintains connecting the first power supply terminal, when the first preset condition occurs.

For example, the switching component 102 is configured to disconnect the power supply to the second processor 130, when a failure of at least one of the second processor 130, the extension device 10, the extension function component 20, and the extension monitoring component 30, occurs. Alternatively, or additionally, the switching component 102 is configured to disconnect the power supply to the second processor 130 when a supply power of the power supply device 170 is lower than a preset value. Therefore, it is possible to prevent the negative effects of the failures of the second processor 130, the extension device 10, the extension function component 20, and the extension monitoring component 30, such as a short circuit or an insufficient power supply, on the functions of the first processor 120, and prioritize the power demand for the defibrillation function, the monitoring function, and the human-machine interaction function.

In some embodiments, the second processor 130 is further configured to, when a second preset condition occurs, acquire and process the data from the defibrillation component 110 and/or the monitoring component 140 to obtain the defibrillation data and/or the monitoring data. Exemplarily, when the first processor 120 fails, the second processor 130 acquires the data from the defibrillation component 110 and/or the monitoring component 140 and processes the same to obtain the defibrillation data and/or the monitoring data. Understandably, the second processor 130 can serve as a backup to the first processor 120 to improve the reliability of the defibrillation device 100.

In some embodiments, the processor state of the second processor 130 includes at least a turn-off state and a working state, and optionally, the processor state of the second processor 130 can also include a low power consumption state. Exemplarily, the second processor 130 acquires the extension device data from the extension device 10, when it is in the working state. The second processor 130 stops acquiring the extension device data from the extension device 10, when it is in the turn-off state or the low power consumption state. Optionally, when the defibrillation device 100 is powered on, the processor state of the second processor 130 can be either in the turn-off state, the working state, or the low power consumption state.

Exemplarily, when the second processor 130 is in the working state, the second processor 130 can also transmit the acquired extension device data to the first processor 120. Alternatively, when the second processor 130 is in the working state, it can also process the acquired extension device data and then transmit the processed extension device data to the first processor 120.

The first processor 120 is further configured to output the defibrillation data and/or the monitoring data through the human-machine interaction component 150. Optionally, when the second processor 130 is in the working state, the first processor 120 is further configured to output the data transmitted by the second processor 130 through the human-machine interaction component 150.

Exemplarily, when the second processor 130 is in the working state, the first processor 120 is further configured to acquire the operation instruction for the extension device 10 through the human-machine interaction component 150 and transmit the operation instruction to the second processor 130. The second processor 130 is configured to control the extension device 10 to execute corresponding extension task according to the operation instruction.

Exemplarily, when the second processor 130 is in the working state, the first processor 120 is further configured to acquire the operation instruction for the second processor 130 through the human-machine interaction component 150 and transmit the operation instruction to the second processor 130. The second processor 130 processes the extension device data acquired from the extension device 10 according to the operation instruction.

Exemplarily, when the second processor 130 is in the working state, the second processor 130 is further configured to transmit the defibrillation data and/or the monitoring data to the target device through the communication component 160; and/or when the second processor 130 is in the working state, the second processor 130 is further configured to transmit the acquired or processed extension device data to the target device through the communication component 160.

Exemplarily, when the second processor 130 is in the working state, the second processor 130 is further configured to transmit the defibrillation data and/or the monitoring data, as well as the acquired or processed extension device data, to the target device through the communication component 160. For example, when the second processor 130 is in the working state, the second processor 130 is further configured to generate the target visual information according to the defibrillation data and/or the monitoring data, as well as the acquired or processed extension device data, and to transmit the target visual information to the target device through the communication component 160. For example, when the second processor 130 is in the working state, the second processor 130 is further configured to transmit the ultrasound image data and/or the laryngoscope image data to the first processor 120, so as to display the ultrasound image and/or laryngoscope image through the human-machine interaction component 150. Additionally, or optionally, when the second processor 130 is in the working state, the second processor 130 is further configured to transmit the ultrasound image data and/or the laryngoscope image data to the target device through the communication component 160. For example, when the second processor 130 is in the working state, the second processor 130 is further configured to process the ultrasonic data and/or the laryngoscope data to generate the ultrasound image data and/or the laryngoscope image data, and to transmit the ultrasound image data and/or the laryngoscope image data to the first processor 120 to display the ultrasound image and/or the laryngoscope image through the human-machine interaction component 150; and/or to transmit the ultrasound image data and/or the laryngoscope image data to the target device through the communication component 160.

Exemplarily, when the second processor 130 is in the working state, the second processor 130 is further configured to acquire the extension device data through at least one of the data reading component, the extension human-machine interaction component 150, and the camera component, and to transmit the extension device data to the target device and/or the first processor 120. For example, when the second processor 130 is in the working state, the second processor 130 is further configured to acquire the feedback information which is transmitted by the target device for extension device data.

Exemplarily, when the second processor 130 is in the working state, the second processor 130 is further configured to acquire data from the extension monitoring component 30 and process the data.

In some embodiments, when the first processor 120 is in a working state, the second processor 130 can be in either of at least two processor states, including a turn-off state or a low power consumption state, as well as a working state. Wherein, when the second processor 130 is in the working state, it acquires the extension device data from the extension device 10.

Optionally, the first processor 120 can switch the processor state of the second processor 130. For example, the first processor 120 can switch the second processor 130 from the turn-off state or the low power consumption state to the working state, or can switch the second processor 130 from the working state to the turn-off state or the low power consumption state. Of course, it is not limited to this, for example, it is possible to control the processor state of the second processor 130 to switch between the turn-off state and the low power consumption state. Exemplarily, the first processor 120 may control the second processor 130 to switch the processor states by transmitting control information to the second processor 130.

Optionally, as shown in FIG. 13, the defibrillation device 100 further includes a third processor 103, which is a processor other than the first processor 120 and the second processor 130. The third processor 103 is capable of switching the processor state of the second processor 130. For example, the third processor 103 of the defibrillation device 100 may be connected with the second processor 130, may also be connected with the first processor 120, or may also be connected with the human-machine interaction component 150. For example, the third processor 103 can switch the second processor 130 from the turn-off state or the low power consumption state to the working state, or can switch the second processor 130 from the working state to the turn-off state or the low power consumption state. Of course, it is not limited to this, for example, it is possible to control the processor state of the second processor 130 to be switched between the turn-off state and the low power consumption state. Exemplarily, the third processor 103 may control the second processor 130 to switch the processor states by transmitting control information to the second processor 130.

Optionally, the second processor can switch the processor state of the second processor. Exemplarily, when the processor state of the second processor 130 is in the low power consumption state or the working state, it is possible to switch the processor state of the second processor 130.

For example, when the second processor 130 is in the low power consumption state, it can be switched to the turn-off state or the working state. Or when the second processor 130 is in the working state, it can be switched to the turn-off state or the low power consumption state.

For example, when the second processor 130 is in the low power consumption state, it can also make autonomous decisions to determine whether to switch to the turn-off state or the working state. For example, the second processor 130 has some data transmission and information processing capabilities in the low power consumption state. For example, preset information such as defibrillation data and/or monitoring data may be transmitted between the first processor 120 and the second processor 130, when the second processor 130 is in the low power consumption state, wherein the monitoring data is obtained by the first processor 120 through processing the data obtained from the monitoring component 140. Of course, it is not limited to this. For example, when the second processor 130 is in the low power consumption state, the second processor 130 can also determine the extension device 10 accessed by the defibrillation device 100 and/or can obtain human-machine interaction instructions through the human-machine interaction component 150. When the second processor 130 is in the low power consumption state, it is possible to make an autonomous decision that whether to switch to the working state or turn-off state according to at least one of the preset information obtained from the first processor 120, the extension device 10 accessed by the defibrillation device 100, and the human-machine interaction instruction.

In some embodiments, the processor state of the second processor 130 can be switched from the turn-off state or the low power consumption state to the working state. For example, the first processor 120 or the third processor switches the processor state of the second processor 130 from the turn-off state or the low power consumption state to the working state. Optionally, the second processor 130 in the low power consumption state can switch its processor state to the working state.

For example, the processor state of the second processor 130 is switched to the working state when at least one of the extension device 10, the extension function component 20, and the extension monitoring component 30 satisfies a first extension start condition. For example, the first processor 120 or the third processor is configured to switch the processor state of the second processor 130 to the working state when the extension device 10 satisfies the first extension start condition. For example, the second processor 130 in the low power consumption state is configured to switch the processor state of the second processor 130 to the working state when the extension device 10 accessed by the defibrillation device 100 satisfies the first extension start condition.

For example, when the defibrillation device 100 is connected with the ultrasonic device 11 and/or the laryngoscope device 12, the processor state of the second processor 130 is switched to the working state, so that the second processor 130 acquires the ultrasound image data and/or the laryngoscope image data, and transmits the acquired ultrasound image data and/or the acquired laryngoscope image data to the first processor 120. When the defibrillation device 100 is not connected with some or all of the extension devices 10 corresponding to the first extension start condition, it is possible not to switch the second processor 130 to the working state. For example, it is also possible to switch the processor state of the second processor 130 from the low power consumption state to the turn-off state. By controlling the start, sleeping, or turn-off of the second processor 130 on demand, it is possible to effectively reduce the power consumption of the defibrillation device 100.

Exemplarily, the processor state of the second processor 130 is switched according to the defibrillation data and/or the monitoring data. The monitoring data is obtained by the first processor 120 through processing the data acquired from the monitoring component 140.

Optionally, the processor state of the second processor 130 is switched to the working state when the defibrillation data and/or the monitoring data satisfy/satisfies a preset second extension start condition. For example, the first processor 120 or the third processor is configured to switch the processor state of the second processor 130 to the working state when the defibrillation data and/or the monitoring data satisfy/satisfies the preset second extension start condition. For example, the second processor 130 in the low power consumption state is configured to switch the processor state of the second processor 130 to the working state when the defibrillation data and/or the monitoring data satisfy/satisfies the preset second extension start condition.

Optionally, when determining, according to ECG, blood oxygen and blood pressure of the patient, that further diagnosis about the situation of the patient needs to be performed through the extension device 10, such as ultrasonic device, laryngoscope, and the likes, the second processor 130 can be switched to the working state so that the second processor 130 can acquire the ultrasound image data and/or the laryngoscope image data. When determining that it is not necessary to diagnose the patient through the extension device 10, the second processor 130 cannot be switched to the working state. For example, the processor state of the second processor 130 can be switched from the low power consumption state to the turn-off state. By controlling the start, sleeping, or turn-off of the second processor 130 on demand, it is possible to effectively reduce the power consumption of the defibrillation device 100.

Exemplarily, the processor state of the second processor 130 is switched to the working state according to a processor start instruction and/or an extension start instruction, and the processor start instruction and/or the extension start instruction are/is acquired through the human-machine interaction component 150. Wherein the processor start instruction is configured to control the second processor 130 to switch to the working state, and the extension start instruction is configured to control the second processor 130 to switch to the working state and to acquire the extension device data from the extension device 10 which corresponds to the extension start instruction.

For example, the first processor 120 or the third processor is configured to acquire the processor start instruction and/or the extension start instruction through the human-machine interaction component 150, and switch the processor state of the second processor 130 to the working state according to the processor start instructions and/or the extension start instruction. For example, the second processor 130 in the low power consumption state can obtain the processor start instruction and/or the extension start instruction through the human-machine interaction component 150, and switch the processor state of the second processor 130 to the working state according to the processor start instruction and/or the extension start instruction.

The user can determine whether it is necessary to start the extension device 10 according to the situation of the patient, and trigger, when necessary, the processor start instruction and/or the extension start instruction through the human-machine interaction component 150 to switch the second processor 130 to the working state.

For example, after the processor start instruction switches the second processor 130 to the working state, the second processor 130 can determine the extension device 10 accessed by the defibrillation device 100, and the human-machine interaction component 150 can output device information of the extension device 10 accessed by the defibrillation device 100. The corresponding extension device 10 can be further controlled and started according to the extension start instruction triggered by the user. So that the second processor 130 acquires the extension device data of the extension device 10 corresponding to the extension start instruction. Of course, it is not limited to this. For example, after the second processor 130 switches to the working state, it is possible to acquire the extension device data from all extension devices 10. Alternatively, the first processor 120 or the second processor 130 in the low power consumption state can control the human-machine interaction component 150 to output the device information of the extension device 10 accessed by the defibrillation device 100, switch the processor state of the second processor 130 to the working state according to the extension startup command triggered by the user, and control the corresponding extension device 10 to start.

Optionally, the human-machine interaction component 150 is further configured to output indication information when the defibrillation data and/or the monitoring data satisfy/satisfies a preset indication condition, and the indication information is configured to indicate the user to operate to trigger the processor start instruction and/or the extension start instruction. The monitoring data is obtained by the first processor 120 through processing the data acquired from the monitoring component 140. For example, the first processor 120, or the third processor, or the second processor 130 which is in the low power consumption state, is further configured to output the indication information through the human-machine interaction component 150 when the defibrillation data and/or the monitoring data satisfy/satisfies the preset indication condition, and the indication information is configured to indicate the user to operate to trigger the processor start instruction and/or the extension start instruction.

For example, when determining, according to ECG, blood oxygen and blood pressure of the patient, that further diagnosis about the situation of the patient needs to be performed through the extension device 10, such as ultrasonic device, laryngoscope, and the likes, the indication information is output, and the user determines whether to start the second processor 130 and the corresponding extension device 10.

In some embodiments, the processor state of the second processor 130 can be switched from the working state to the turn-off state or the low power consumption state. For example, the first processor 120 or the third processor switches the processor state of the second processor 130 from the working state to the turn-off state or the low power consumption state. Optionally, the second processor 130 in the working state can switch its processor state to the turn-off state or the low power consumption state. The second processor 130 in the turn-off state or low power consumption state, can reduce the power consumption of the defibrillation device 100, and can also reduce the negative effect on the first processor 120, thus improving the reliability of the first processor 120 during performing defibrillation task.

For example, when at least one of the extension device 10, the extension function component 20, and the extension monitoring component 30 satisfies a preset first extension turn-off condition, and/or the defibrillation data and/or the monitoring data satisfy/satisfies a preset second extension turn-off condition, the processor state of the second processor 130 is switched to the turn-off state or the low power consumption state to reduce the power consumption of the defibrillation device 100.

Optionally, the processor state of the second processor 130 is switched to the turn-off state or the low power consumption state when at least one of the extension device 10, the extension function component 20, and the extension monitoring component 30 satisfies the preset first extension turn-off condition. For example, when the defibrillation device 100 is not connected with the ultrasonic device 11 and/or the laryngoscope device 12, the processor state of the second processor 130 is switched to the turn-off state or the low-power consumption stat. Optionally, when the defibrillation device 100 is not connected with some or all of the extension devices 10 corresponding to the first extension start condition, the processor state of the second processor 130 is switched to the turn-off state or the low power consumption state.

Optionally, the processor state of the second processor 130 is switched to the turn-off state or the low power consumption state when the defibrillation data and/or the monitoring data satisfy/satisfies a preset second extension turn-off condition. For example, the first processor 120 or the third processor is further configured to switch the processor state of the second processor 130 to the turn-off state or the low power consumption state when the defibrillation data and/or the monitoring data satisfy/satisfies the preset second extension turn-off condition. For example, the second processor 130 in the working state is configured to switch the processor state of the second processor 130 to the turn-off state or the low power consumption state when the defibrillation data and/or the monitoring data satisfy/satisfies the preset second extension turn-off condition.

Optionally, when determining, according to ECG, blood oxygen and blood pressure of the patient, that it is not necessary to diagnose the patient through the extension device 10, the second processor 130 is switched to the turn-off state or the low power consumption state to reduce the power consumption of the defibrillation device 100.

Exemplarily, the processor state of the second processor 130 is switched to the turn-off state or the low power consumption state according to a turn-off instruction, which is acquired through the human-machine interaction component 150. For example, the first processor 120 or the third processor is further configured to switch the processor state of the second processor 130 to the turn-off state or the low power consumption state according to the turn-off instruction when the turn-off instruction is acquired through the human-machine interaction component 150. For example, the second processor 130 in the working state is further configured to switch the processor state of the second processor 130 into to the turn-off state or the low power consumption state according to the turn-off instruction when receiving the turn-off instruction through the human-machine interaction component 150.

The user can determine whether it is necessary to start the extension device 10 according to the situation of the patient, and trigger the turn-off instruction through the human-machine interaction component 150 when it is not necessary, so as to switch the second processor 130 to the turn-off state or the low power consumption state.

Optionally, when determining, according to ECG, blood oxygen and blood pressure of the patient, that further diagnosis about the situation of the patient needs to be performed through the extension device 10, such as ultrasonic device, laryngoscope, and the likes, corresponding suggestions can be outputted through the human-machine interaction component 150. The user can determine whether to start the extension device 10 according to the indication and the situation of the patient.

The defibrillation device provided in the embodiment of the present disclosure includes a defibrillation component, a first processor, and a second processor. Wherein the defibrillation component is configured to perform a defibrillation task, the first processor is configured to acquire data from the defibrillation component and process said data to obtain defibrillation data; and the second processor is configured to acquire extension device data from an extension device, the second processor is connected with the first processor, and the second processor and the first processor are capable of transmitting preset information. In this defibrillation device, the defibrillation function is performed by the first processor, and the function of the extension device is performed by the second processor, such that the functional isolation between the defibrillation task and the extended task is achieved. The failure of the second processor or extension device does not affect the performance of the core defibrillation rescue function, so that the defibrillation device has high safety.

In some embodiments, the defibrillation device can switch the processor state of the second processor, such as switch the processor state of the second processor to the working state when it is necessary to extend the functionality of the device, so that the second processor can obtain extension device data from the extension device. The defibrillation device can also switch the processor state of the second processor to the turn-off state or the low power consumption state to reduce the power consumption of the defibrillation device, when it is not necessary to extend the functionality of the device. This is also possible to reduce the negative effect of the second processor, the extension device on the function of the first processor, and improve the reliability of the defibrillation device.

An defibrillation device of an embodiment of this disclosure is described below with reference to FIGS. 9A to 9C. The defibrillation device includes a defibrillation component 110, at least two processors, and a display 130. Wherein the defibrillation component 110 is configured to perform a defibrillation task. The at least two processors include at least a first processor 120A and a second processor 120B. In the first state, the first processor 120A is at least configured to acquire data from the defibrillation component 110 and process said data to obtain defibrillation data, and generate at least one piece of basic display information based on the defibrillation data. The second processor 120B is at least configured to acquire data from at least one first extension device and process said data to obtain first extension device data, and generate at least one piece of first extension display information based on the first extension device data. At least one of the processors includes a display fusion module. In the first state, the display fusion module is configured to receive the at least one piece of basic display information which is generated by the first processor 120A and the at least one piece of first extension display information which is generated by the second processor 120B, and fuse the at least one piece of basic display information and at least one piece of first extension display information to generate terminal display information. The display 130 is configured to output terminal display information.

In the prior arts, when defibrillation devices fuse data from extension devices, they firstly gather the defibrillation data and the data from the extension device into a main processor or main process, and then uniformly process the data to generate terminal display information by the main processor or main process and output the terminal display information to the display. In contrast, the defibrillation device in the embodiment of this disclosure uses a display fusion method to generate the terminal display information, such that the basic display information and extension display information never mutually affect each other and better risk isolation effect is achieved. When connecting a new extension device, just the new extension display information is generated and then fused with the original display information, without modifying the original display information, which makes the scalability more flexible.

The processor can be a central processing unit (CPU), other general-purpose processor, digital signal processor (DSP), application specific integrated circuit (ASIC), field programmable gate array (FPGA), or other programmable logic device, discrete gate, or transistor logic device, discrete hardware component, etc. The general-purpose processor may be a microprocessor, or the processor may also be any conventional processor, etc. Further, the defibrillation device further includes a memory. The memory is at least configured to store defibrillation data acquired during defibrillation. The memory also stores program code, and the processor is configured to call the program code in the memory to perform the functions described below. The memory may include high-speed random access memory, and may also include nonvolatile memory, such as hard disk, internal storage, plug-in hard disk, smart memory card, flash memory card, and the likes.

The defibrillation component 110 is configured to perform a defibrillation task. The defibrillation task refers to applying a pulse current to a heart to perform an electric shock to treat and eliminate arrhythmia and restore the heart to a sinus rhythm. Exemplarily, the defibrillation component 110 includes a defibrillation electrode, a charge circuit, a discharge circuit, a power supply, and the likes. The defibrillation electrode is configured to attach to a chest surface of a patient, thereby releasing a defibrillation current to stimulate human body. In some embodiments, the defibrillation electrode can also be configured to acquire both ECG signal and impedance information. The charge circuit is configured to receive and store electrical energy. When a patient is subjected to an electric shock, the electrical energy stored in the charge circuit is loaded onto the defibrillation electrode through the discharge circuit, thus transmitting a high-voltage pulse signal to the patient to help the patient restore normal heart rate. The power supply is configured to provide electrical energy for the charge circuit.

The defibrillation component 110 is at least connected with the first processor 120A, and the first processor 120A is at least configured to acquire data from the defibrillation component 110 and process said data to obtain defibrillation data. In some embodiments, the first processor 120A is further configured to control the defibrillation component 110 to perform the defibrillation task. Exemplarily, a mode used by the defibrillation device can be an automatic defibrillation mode or a manual defibrillation mode. In the automatic defibrillation mode, the first processor 120A can also be configured to analyze the ECG signal, such as to analyze whether the ECG signal contains a defibrillation rhythm. When the first processor 120A obtains a detection result that the ECG signal contains a defibrillation rhythm, it transmits a defibrillation instruction to the defibrillation component 110 to perform charging and discharging. In the manual defibrillation mode, the defibrillation component 110 can perform the defibrillation task based on user operations.

The defibrillation device further includes a display 130 which is configured to provide a visual display output to the user. For example, in the first state, the display 130 is configured to output the terminal display information generated by fusing the basic display information and the first extension display information. Exemplarily, the display 130 can be implemented as a touch display, or a display with an input panel, that is, the display 130 can serve as an input/output device. Of course, the display 130 can also output the basic display information alone, or output the extension display information alone. For example, when the defibrillation device is not connected with the extension device, the display 130 can output the basic display information alone.

Exemplarily, the basic display information, which is generated by the first processor 120A, includes at least defibrillation display information. The first processor 120A acquires data from the defibrillation component 110, processes said data to obtain defibrillation data, and generates the defibrillation display information at least based on the defibrillation data. Exemplarily, the defibrillation data includes defibrillation energy, number of shocks, and the likes. The defibrillation display information can also include patient information, power information, operational controls, and other information that users of other defibrillation devices need to view. The defibrillation display information may be display information corresponding to the automatic defibrillation mode or display information corresponding to the manual defibrillation mode.

In some embodiments, the defibrillation device further includes a monitoring component for performing a monitoring task. The monitoring component is configured to monitor various parameters of patient, including at least ECG parameter, and optionally, blood oxygen saturation, respiratory rate, noninvasive blood pressure, invasive blood pressure, pulmonary artery pressure, intracranial pressure, carbon dioxide concentration, cardiac output, etc. For example, the monitoring component can support hot plugging and has a plug-in interface that matches the plug-in slot of the defibrillation device. The monitoring component can be inserted into the defibrillation device, or can be removed from the defibrillation device and inserted into the monitoring device or other medical device. The first processor 120A is further configured to acquire data from the monitoring component 110, process said data to obtain monitoring data, and generate basic display information at least based on the defibrillation data and the monitoring data.

When generating the basic display information based on the defibrillation data and the monitoring data, the first processor 120A can comprehensively process the defibrillation data and the monitoring data to generate the basic display information. Optionally, the first processor 120A can also generate defibrillation display information based on the defibrillation data, and generate monitoring display information based on monitoring data, and then input the defibrillation display information and the monitoring display information into the display fusion module respectively. The display fusion module receives the defibrillation display information and the monitoring display information, and fuses the defibrillation display information and the monitoring display information to generate the basic display information. When using the display fusion method to generate basic display information, the first processor 120A runs different processes to generate the defibrillation display information and the monitoring display information, and the processes are isolated from each other. Changes in the defibrillation data never affect the monitoring display information, and changes in the monitoring data never affect the defibrillation display information. When there is an error in the monitoring display information, the display 130 can also output the defibrillation display information normally.

Furthermore, the defibrillation device further includes a communication module which is configured to establish a communication connection with the extension device to acquire data from the extension device through the communication connection. The second processor 120B is configured to acquire data from the first extension device, process said data to obtain the first extension device data, and to generate at least one piece of first extension display information based on the first extension device data. Exemplarily, since the extension device itself typically has a data processing function, the data obtained through the communication module can be logically processed data. Of course, the data obtained through the communication module can also be raw data, which is logically processed by the processor of the defibrillation device.

Defibrillation devices are high-risk medical devices that require significant safety assessments to add new applications or functions to a single processor. In the embodiment of this disclosure, the second processor 120B is responsible for generating the first extension display information corresponding to the first extension device. Failure of the second processor 120B or error in the first extension display information neither affects the normal display of the basic display information, nor affects the core defibrillation rescue function of the defibrillation device, so it is safer and more convenient to extend and improve performance at the second processor 120B. When it is necessary to connect a new first extension device and display its information, it is only necessary to deploy the corresponding software module in the second processor 120B, which has stronger scalability.

Exemplarily, the data acquired by the second processor 120B from the first extension device can be real-time monitoring data or historical data. For example, when the first extension device is a monitoring device, the data obtained from the monitoring device can be real-time monitoring data or can include historical monitoring data. When the monitoring data is real-time monitoring data, the first extension display information may include values, waveforms, and the like of the real-time monitoring data. When the monitoring data is historical monitoring data, the first extension display information may include statistical values, trend charts, and the likes of historical monitoring data.

Exemplarily, the first extension device includes at least one of the following: ultrasound device, endoscope device, camera device, monitoring device, ventilator, compression machine, and infusion pump. Wherein the first extension display information corresponding to the ultrasound device includes at least an ultrasound image. The first extension display information corresponding to the endoscope device includes at least an endoscope image. The first extension display information corresponding to the camera device includes at least a video image or a static image which is captured by the camera device. The first extension display information corresponding to the monitoring device includes at least monitoring value of physiological parameter. The first extension display information corresponding to the ventilator includes ventilation parameter of patient. The first extension display information corresponding to the compression machine includes a compression frequency, compression depth, and the likes. The first extension display information corresponding to the infusion pump includes an infusion flow rate, pressure, drug name, and the likes. When connecting at least two first extension devices, the second processor 120B can run different processes to generate the first extension display information corresponding to the different first extension devices.

Exemplarily, the communication connection between the second processor 120B and the first extension device includes, but is not limited to, a plug-in connection. The communication module based on plug-in connection includes a plug-in slot that supports hot plugging. The plug-in slot matches the interface of the extension device, and includes a mechanical structure that can accommodate other components, a data transmission interface for data interaction with the extension device, and a power interface for powering the extension device. The plug-in slot is connected with the second processor 120B and can transmit data from the first extension device inserted into the plug-in slot to the second processor. In some embodiments, instructions of the second processor 120B can also be transmitted to the extension device. In addition to plug-in connection, the communication connection method between the second processor 120B and the first extension device can also include a wireless connection or wired connection. The wireless connection can specifically include infrared connection, Bluetooth connection, Wi-Fi connection, WMTS connection, 4G connection, 5G connection, and so on.

At least one of the processors includes a display fusion module, which is configured to fuse at least one piece of basic display information and at least one piece of extension display information to generate terminal display information, and output the terminal display information to the display 130 for display. Medical personnel can view the data of the defibrillation device and the data of the first extension device on the display 130 of the defibrillation device, without the need to separately monitor the monitoring device and the first extension device, thus improving the work efficiency of medical personnel.

In the embodiment of this disclosure, the basic display information which is outputted by the first processor 120A and the first extension display information which is outputted by the second processor 120B are fused by the display fusion module. The first processor 120A and the second processor 120B do not have complex data interactions, and each generates display information, and the generated display information is fused by the display fusion module. The isolation between processes is more completely, which can better ensure the safety of the defibrillation device. Similarly, the scalability of defibrillation device is also more flexible. When adding new extension devices, it is only necessary to add new software units to the second processor 120B to generate corresponding extension display information, and then place the extension display information into the terminal display information through the display fusion module without modifying the original software units.

In some embodiments, the display fusion module superimposes at least one piece of basic display information and at least one piece of first extension display information to generate the terminal display information. For example, the basic display information can be used as the background, while the first extension display information can be used as the foreground, the size of the foreground can be scaled appropriately as needed, and then the foreground is placed at an appropriate position in the background, and finally the basic display information and the first extension display information are superimposed and outputted. Alternatively, the display fusion module can join at least one piece of basic display information and at least one piece of first extension display information to generate the terminal display information.

In some embodiments, the first processor 120A can generate one piece of basic display information, and the second processor 120B can generate one piece of first extension display information. That is, the one piece of basic display information generated by the first processor 120A can be one complete user interface. The one piece of first extension display information generated by the second processor 120B can be one complete user interface. The display fusion module can fuse the two complete user interfaces. Alternatively, the first processor 120A is configured to generate at least two pieces of basic display information, and the second processor 120B is configured to generate at least two pieces of first extension display information. For example, the at least two pieces of basic display information generated by the first processor 120A may include defibrillation display information and monitoring display information, and the at least two pieces of first extension display information generated by the second processor 120B may include the first extension display information corresponding to the camera device, the first extension display information corresponding to the ultrasound device, and the likes. The display fusion module fuses multiple pieces of display information.

In some embodiments, the display 130 is further configured to receive a setting instruction for the defibrillation data and transmit the setting instruction to the first processor 120A. The first processor 120A sets the defibrillation data based on the received setting instruction for the defibrillation data. The display 130 is further configured to receive a setting instruction for the first extension device data and transmit the setting instruction to the second processor 120B. The second processor 120B forwards the setting instruction for the first extension device data to the first extension device through the communication connection with the first extension device. Medical personnel can control the defibrillation device and the first extension device through the display interface of the defibrillation device, thus further improving the work efficiency of medical personnel.

Figure 9A:
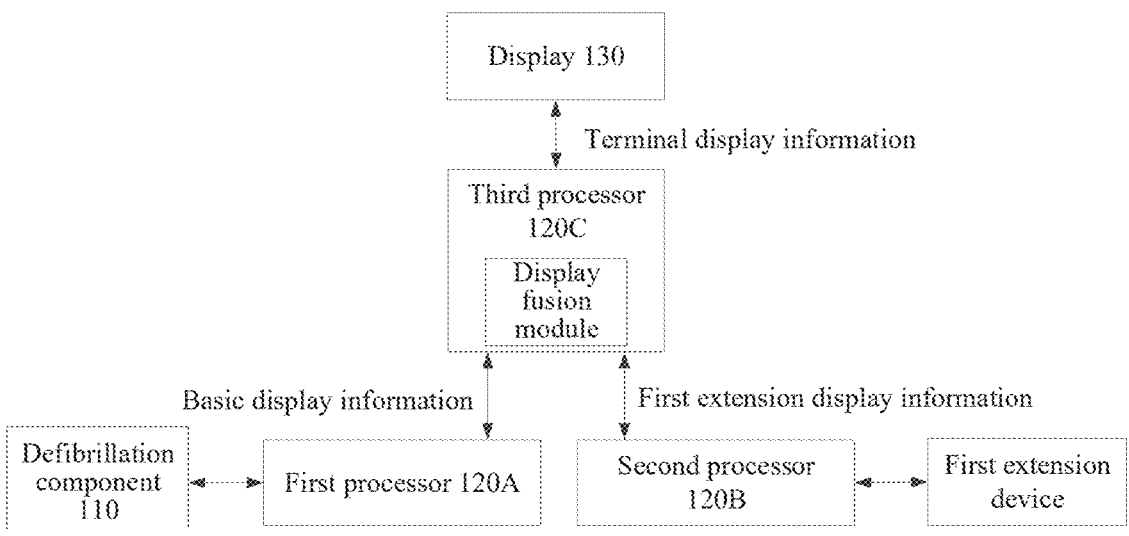
FIGS. 9A-9C illustrate a structural block diagram of a defibrillation device according to some embodiments of this disclosure.

As shown in FIG. 9A, the display fusion module can be included in a separate third processor 120C. The third processor 120C is configured to receive at least one piece of basic display information which is generated by the first processor 120A and at least one piece of first extension display information which is generated by the second processor 120B, and fuse the at least one piece of basic display information and the at least one piece of first extension display information to generate the terminal display information. The third processor 120C is further configured to transmit the terminal display information to the display 130. The third processor 120C may be a hardware display fusion device dedicated to display fusion, such as an FPGA hardware display fusion device. The hardware display fusion device has the advantages of good real-time performance, fast processing speed, high flexibility, and can reduce data interaction between the first processor 120A and the second processor 120B.

Figure 9B:
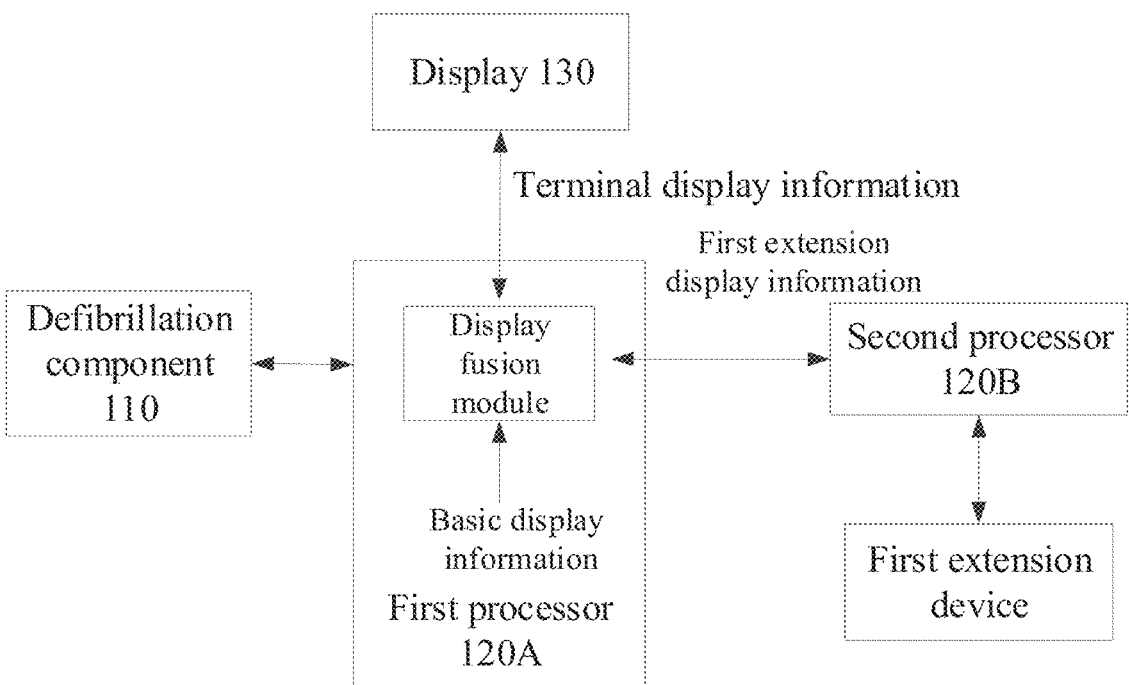

Alternatively, as shown in FIG. 9B, the first processor 120A includes the display fusion module. The first processor 120A receives the first extension display information generated by the second processor 120B, inputs the first extension display information and the basic display information which is generated by the first processor 120A itself into the display fusion module, and the display fusion module fuses the basic display information and the first extension display information to generate terminal display information. The first processor 120A further transmits the terminal display information to the display 130. Setting the display fusion module in the first processor 120A eliminates the need to add new hardware display fusion devices and reduces hardware costs.

Figure 9C:
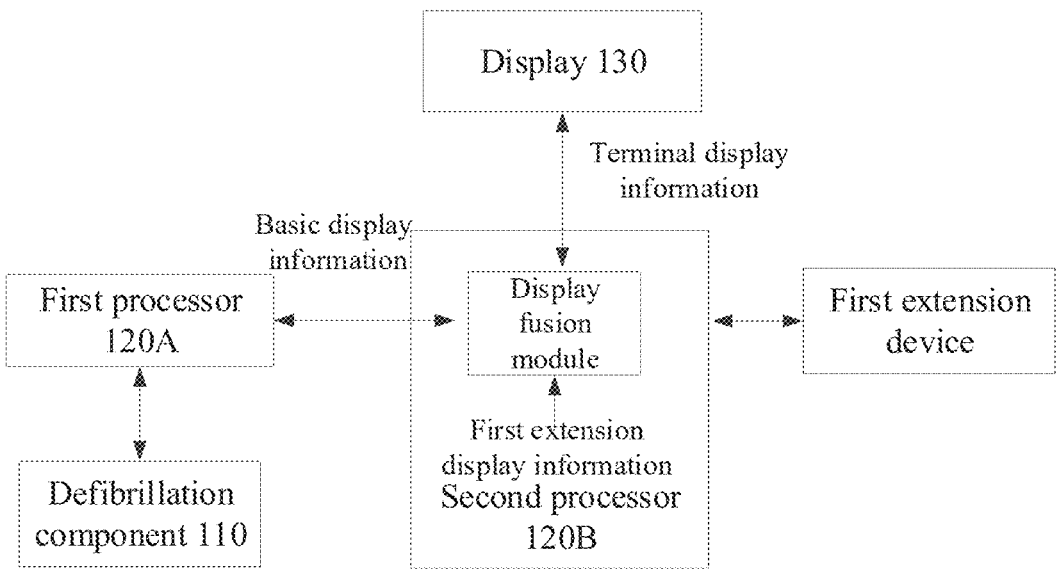

Alternatively, as shown in FIG. 9C, the second processor 120B includes the display fusion module. The second processor 120B receives the basic display information which is generated by the first processor 120A, inputs the basic display information and the first extension display information which is generated by the second processor 120B itself into the display fusion module, and the display fusion module fuses the basic display information and the first extension display information to generate terminal display information. The second processor 120B further transmits the terminal display information to the display 130. In the example of FIG. 9C, the first processor 120A does not need to receive data from the second processor 120B, but only needs to transmit the basic display information to the second processor 120B for display fusion, thus improving the security of the first processor 120A.

As described above, the first processor 120A is mainly configured to generate the basic display information of the defibrillation device. In addition, the first processor 120A can also be configured to acquire the second extension device data from at least one second extension device, and generate at least one piece of second extension display information based on the second extension device data. Specifically, the first processor 120A can create different processes that generate the basic display information and the second extension display information respectively, and the processes are independent of each other. The generation of the basic display information and the generation of the second extension display information never affect each other. The display fusion module is further configured to receive the at least one piece of second extension display information which is generated by the first processor 120A, and fuse the at least one piece of basic display information, the at least one piece of first extension display information and the at least one piece of second extension display information to generate the terminal display information. When the second processor 120B fails, the first processor 120A can also share a portion of the extension display function. The second extension device may be a device with a higher frequency of use, or a device with higher security, such as a monitoring device, etc.

In some embodiments, the first processor 120A is further configured to control the defibrillation component to perform the defibrillation task. Since the first extension display information is generated by the second processor 120B, the isolation between the first processor 120A and the second processor 120B is good, thereby ensuring that the generation of the first extension display information does not affect the normal execution of the defibrillation task.

Unlike the first state described above, in a second state, the first processor 120A acquires data from the defibrillation component and processes said data to obtain the defibrillation data, but docs not generate the basic display information. Exemplarily, the first processor 120A is configured to create a first process and a second process, and the first process is configured to logically process the data acquired from the defibrillation component to obtain the defibrillation data. The second process is configured to generate the basic display information based on the defibrillation data. The first process and the second process are independent of each other and interact with each other through the interaction interface between the processes. When the second process encounters an error and cannot generate the basic display information, the first process can continue to generate the defibrillation data without causing data loss due to the display error.

Similarly, in a third state, the second processor 120B acquires data from the first extension device and process said data to obtain the first extension device data, but does not generate the first extension display information. Exemplarily, the second processor 120B is configured to create a third process and a fourth process, wherein the third process is configured to logically process the data acquired from the first extension device to obtain the first extension device data, and the fourth process is configured to generate the at least one piece of first extension display information based on the first extension device data. The third process and the fourth process are independent of each other and interact with each other through the interaction interface between the processes. When the fourth process encounters an error and cannot generate the first extension display information, the third process can continue to generate the first extension device data.

For example, in a fourth state, the display fusion module is further configured to fuse the at least one piece of basic display information and abnormal display information to generate the terminal display information, and the abnormal display information is configured to indicate that the at least one piece of first extension display information and/or the at least one piece of second extension display information are/is abnormal. If the data is processed concentratedly to generate the terminal display information, when the first extension display information and/or the second extension display information are/is abnormal, the terminal display information fails. The embodiment of this disclosure uses a display fusion method to generate the terminal display information. In this way, when the first extension display information and/or the second extension display information are/is abnormal, the terminal display information can still be outputted. It is only necessary to indicate that the first extension display information and/or the second extension display information are/is abnormal while displaying the basic display information normally, which is safer for the basic defibrillation function and defibrillation display function of the defibrillation device.

Figure 10:
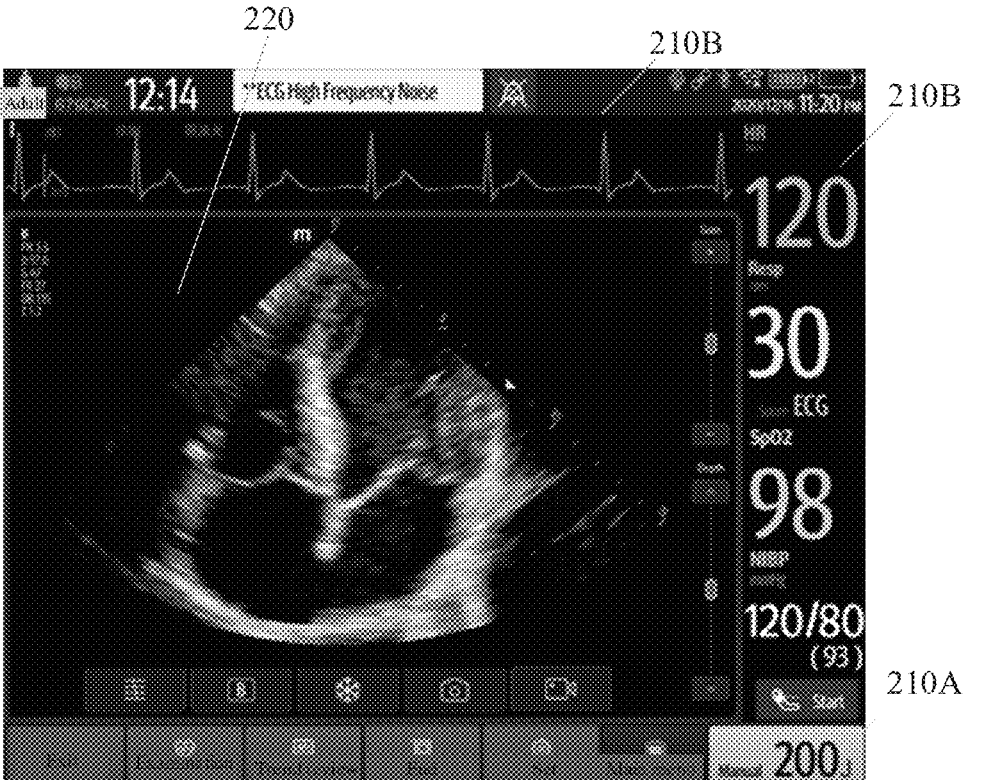
FIG. 10 illustrates a schematic diagram of terminal display information according to some embodiments of this disclosure.

Exemplarily, referring to FIG. 10, the terminal display information, when the first extension device is an ultrasound device, is shown. In the example of FIG. 10, the terminal display information includes basic display areas 210A and 210B which correspond to the basic display information, and an extension display area 220 which corresponds to the extension display information. In the first state, the basic display information is displayed in the basic display areas 210A and 210B, and the first extension display information is displayed in the extension display area 220. The user can view the display information of different devices through different areas. The first extension display information shown in FIG. 10 includes at least an ultrasound image, and further includes operational controls related to the ultrasound device for receiving control instructions for the ultrasound device, such as freeze controls, mode switch controls, and the likes.

In the fourth state, the first extension display information is abnormal, and the first extension display information cannot be normally displayed in the extension display area 220. At this time, the extension display area 220 is configured to display the abnormal display information. The abnormal display information can be grayed output, or in the form of text for indicating that the extension display information is abnormal. While the extension display area 220 displays the abnormal display information, the basic display areas 210A and 210B can display the basic display information normally without affecting the user to view the basic display information.

The basic display area shown in FIG. 10 further includes a defibrillation display area 210A and a monitoring display area 210B. The defibrillation display area 210A is configured to display defibrillation display information, and the monitoring display area 210B is configured to display monitoring display information. The defibrillation display information may include defibrillation data or may further include operational controls related to the defibrillation device. The monitoring display information includes monitoring values of physiological parameters. When the basic display information is generated by fusing the defibrillation display information and the monitoring display information based on the display fusion module, if there is an error in the monitoring display information, the monitoring display area 210B can display the abnormal prompt information to indicate that there is an error in the monitoring display information. At this time, the defibrillation display area 210A can normally output the defibrillation display information.

In summary, the defibrillation device in embodiments of this disclosure uses a display fusion method to generate terminal display information, such that the basic display information and the extension display information never mutually affect each other and better risk isolation effect is achieved. When connecting a new extension device, just the new extension display information is generated and then fused with the original display information, without modifying the original display information, which makes the scalability more flexible.

Another aspect of embodiments of this disclosure provides a medical device including a basic component, at least one processor and a display. The basic component is configured to perform a basic medical function. In a first state, the at least one processor is configured to acquire data from the basic component, process said data to obtain basic data, generate at least one piece of basic display information based on the basic data; wherein the at least one processor is further configured to acquire data from at least one first extension device, process said data to obtain first extension device data, and generate at least one piece of first extension display information based on the first extension device data. The at least one processor includes a display fusion module. Wherein in the first state, the display fusion module is configured to fuse the at least one piece of basic display information and at least one piece of extension display information to generate terminal display information, wherein the at least one piece of extension display information includes at least one piece of first extension display information. In a fourth state, the display fusion module is further configured to fuse the at least one piece of basic display information and abnormal display information to generate the terminal display information, wherein the abnormal display information is configured to indicate that the at least one piece of first extension display information is abnormal. The display is configured to output the terminal display information.

The medical device of this embodiment uses a display fusion method to generate terminal display information. If the data is processed concentratedly to generate the terminal display information, when the first extension display information and/or the second extension display information are/is abnormal, the terminal display information fails. The embodiment of this disclosure uses a display fusion method to generate the terminal display information. In this way, when the first extension display information is abnormal, the terminal display information can still be outputted. It is only necessary to indicate that the first extension display information is abnormal while displaying the basic display information normally, which is safer for the basic medical function of the medical device.

In some embodiments, as illustrated in FIG. 11A, the at least one processor includes a first processor 320A, which is at least configured to acquire data from the basic component 310, process said data to obtain basic data, and generate at least one piece of basic display information based on the basic data. The first processor 320A is further configured to acquire data from at least one first extension device, process said data to obtain first extension device data, and generate at least one piece of first extension display information based on the first extension device data. The display fusion module fuses the basic display information and the first extension display information which are generated by the first processor 320A, and outputs them to the display 330 for display.

Specifically, the first processor 320A can create different processes to generate the basic display information and the first extension display information, and the basic display information and the first extension display information are fused by a display fusion module. The processes are isolated from each other without complex data interaction. Changes in the basic data never affect the first extension display information, and changes in the data from the first extension device never affect the basic display information. Similarly, the scalability of medical devices is also more flexible. When adding new extension devices, it is only necessary to add a new software unit to the first processor 320A to generate corresponding extension display information, and then place it onto the terminal display information through the display fusion module. There is no need to modify the original software unit, making the scalability more flexible.

In one embodiment, continue referring to FIG. 11A, the first processor 320A includes the display fusion module, which can be a software unit provided in the first processor 320A. The first processor 320A is further configured to transmit the terminal display information to the display 330. Using a software display fusion device can reduce hardware costs and reduce the complexity of hardware structures.

In another embodiment, as shown in FIG. 11B, the at least one processor further includes a third processor 320C, and the third processor 320C includes the display fusion module, that is, the display fusion module can be a hardware display fusion device. The third processor 320C is configured to transmit the terminal display information to the display 330. The third processor 320C may be a hardware display fusion device dedicated to display fusion, such as an FPGA hardware display fusion device. The hardware display fusion device has the advantages of good real-time performance, fast processing speed, and high flexibility.

The medical device of the embodiment of this disclosure can be a defibrillation device, and the basic component 310 includes a defibrillation component of the defibrillation device for performing the defibrillation task. The basic data includes defibrillation data. The medical device of the embodiment of this disclosure can also include a monitoring device, an ultrasound device, a ventilator, and the likes. When the medical device is a monitoring device, the basic component 310 is configured to perform a monitoring function. When the medical device is an ultrasound device, the basic component 310 is configured to perform an ultrasound data acquisition function. When the medical device is a ventilator, the basic component 310 is configured to perform a respiratory support function.

In some embodiments, the defibrillation device further includes a monitoring component for performing a monitoring task. The first processor 320A is further configured to acquire data from the monitoring component, process said data to obtain monitoring data, and generate at least one piece of basic display information based on the defibrillation data and the monitoring data. When generating the basic display information based on the defibrillation data and the monitoring data, the first processor 320A can comprehensively process the defibrillation data and monitoring data to generate basic display information. Alternatively, the first processor 320A generates the defibrillation display information based on the defibrillation data, and generates the monitoring display information based on the monitoring data. The display fusion module receives the defibrillation display information and the monitoring display information which are generated by the first processor 320A, fuses the defibrillation display information and the monitoring display information, and generates the basic display information. Therefore, the mutual influence between the defibrillation display information and the monitoring display information can be avoided, and the defibrillation display information can also be displayed normally when the monitoring display information is abnormal. In some embodiments, the first extension device includes at least one: an ultrasound device, a monitoring device, an endoscope device, a camera device, a ventilator, a compression machine, and an infusion pump. Wherein the first extension display information corresponding to the monitoring device includes at least a monitoring value of physiological parameter. The first extension display information corresponding to the ultrasound device includes at least an ultrasound image. The first extension display information corresponding to the endoscope device includes at least an endoscope image. The first extension display information corresponding to the camera device includes at least a video image or a static image which is captured by the camera device. The first extension display information corresponding to the ventilator includes a ventilation parameter of patient. The first extension display information corresponding to the compression machine includes a compression frequency, compression depth, and the likes. The first extension display information corresponding to the infusion pump includes an infusion flow rate, pressure, drug name, and the likes. The first processor 320A can respectively acquire data from at least two first extension display devices and run different processes to generate at least two pieces of first extension display information respectively, thus avoiding mutual influence between the different pieces of first extension display information corresponding to different first extension display devices.

In addition to generate the basic display information, the first processor 320A can also be configured to control the basic component 310 to perform the basic medical function. Because the first processor 320A uses different processes which are isolated from each other to generate the basic display information and the first extension display information, the processes do not affect each other and have high security, thereby ensuring that the generation of the first extension display information does not affect the normal execution of the basic medical function.

In summary, the medical device of this embodiment uses a display fusion method to generate terminal display information. When the first extension display information is abnormal, the terminal display information can still be output. It is only necessary to indicate that the first extension display information is abnormal while displaying the basic display information normally, which is safer for the basic medical function of the medical device.

A further aspect of an embodiment of this disclosure provides a display method for medical data 400 which is shown in FIG. 12, including following steps:

in step S410, acquiring basic data, and at least generating at least one piece of basic display information based on the basic data;

in step S420, acquiring first extension device data, and generating at least one piece of first extension display information based on the first extension device data;

in step S430, in a first state, fusing the at least one piece of basic display information and at least one piece of extension display information to generate terminal display information, wherein the at least one piece of extension display information includes the at least one piece of first extension display information; and in step S440, outputting the terminal display information.

The display method for medical data in embodiments of this disclosure can be applied to the medical device, as well as other devices. Specifically, the basic data can be obtained by acquiring data from the basic component and processing said data. The first extension device data can be obtained by acquiring data from the at least one first extension device and processing said data. Exemplarily, a first processor of the medical device can acquire data from the basic component and process said data to obtain the basic data, and then generate the basic display information based on the basic data. A second processor of the medical device can acquire data from the at least one first extension device and process said data to obtain the first extension device data, and then generate the first extension display information based on the first extension device data. Alternatively, the first processor of the medical device can generate the basic display information and first extension display information, respectively.

In some embodiments, when the display method for medical data is applied to the defibrillation device, the basic data includes defibrillation data of the defibrillation device. The display method for medical data 400 further includes acquiring monitoring data, and generating the at least one piece of basic display information based on the defibrillation data and the monitoring data. Exemplarily, generating the at least one piece of basic display information based on the defibrillation data and the monitoring data includes generating defibrillation display information based on the defibrillation data, generating monitoring display information based on the monitoring data; and fusing the defibrillation display information and the monitoring display information and generating the basic display information.

In some embodiments, the display method for medical data 400 further includes in a fourth state, fusing the at least one piece of basic display information and abnormal display information to generate the terminal display information, wherein the abnormal display information is configured to indicate that the at least one piece of first extension display information is abnormal. The display method for medical data in the embodiment of this disclosure uses a display fusion method to generate the terminal display information. In this way, when the first extension display information is abnormal, the terminal display information can still be output. It is only necessary to indicate that the first extension display information is abnormal while displaying the basic display information normally, which has higher security for the basic medical function and basic display function of the medical device.

The display method for medical data 400 in embodiments of this disclosure use a display fusion method to generate the terminal display information, such that the basic display information and extension display information never mutually affect each other and better risk isolation effect is achieved. When connecting a new extension device, just the new extension display information is generated and then fused with the original display information, without modifying the original display information, which makes the scalability more flexible. The display method for medical data 400 in the embodiment of this disclosure can be implemented by the medical device described above. More specific details can be referred to above, and are not described here.

Although exemplary embodiments have been described herein with reference to the accompanying drawings, it should be understood that the above exemplary embodiments are merely illustrative and are not intended to limit the scope of the present disclosure to this extent. Those skilled in the art can make various changes and modifications therein without departing from the scope and spirit of the present disclosure. All these changes and modifications are intended to be included within the scope of the present disclosure as claimed in the appended claims.

Those skilled in the art can realize that the units and algorithm steps of each example described in connection with the embodiments disclosed herein can be implemented in electronic hardware, or a combination of computer software and electronic hardware. Whether these functions are performed in hardware or software depends on the specific application and design constraints of the technical solution. Those skilled in the art can use different methods to achieve the described functions for each specific application, but such implementation should not be considered beyond the scope of this disclosure.

In the several embodiments provided by this disclosure, it should be understood that the disclosed devices and methods can be implemented in other ways. For example, the device embodiments described above are only illustrative. For example, the division of the units is only a logical function division. In actual implementation, there can be other division methods, such as multiple units or components that can be combined or integrated into another device, or some features that can be ignored or not implemented.

This disclosure herein provide a large number of specific details. However, it is understood that embodiments of this disclosure can be practiced without these specific details. In some examples, well-known methods, structures, and techniques are not shown in detail in order not to obscure the understanding of this disclosure.

Similarly, it should be understood that, in order to simplify the present disclosure and assist in understanding one or more aspects of the present disclosure, in the description of exemplary embodiments of the present disclosure, various features of the present disclosure are sometimes grouped together into a single embodiment, diagram, or description thereof. However, the method of this disclosure should not be interpreted as reflecting the intention that the claimed application requires more features than those explicitly documented in each claim. More specifically, as reflected in the corresponding claims, the inventive point of the present disclosure is that it is possible to solve the corresponding technical problem with fewer than all features of a single disclosed embodiment. Therefore, the claims that follow the specific embodiment are hereby explicitly incorporated into the specific embodiment, wherein each claim itself serves as a separate embodiment of the present disclosure.

Those skilled in the art can understand that, except for the mutual exclusion between features, any combination can be configured to combine all features disclosed in this disclosure (including accompanying claims, abstracts, and drawings), as well as all processes or units of any method or device disclosed. Unless otherwise explicitly stated, each feature disclosed in this disclosure (including accompanying claims, abstracts, and drawings) may be replaced by alternative features that provide the same, equivalent, or similar purpose.

In addition, those skilled in the art can understand that although some embodiments described herein include certain features included in other embodiments rather than other features, the combination of features of different embodiments means that they are within the scope of the present disclosure and form different embodiments. For example, in the claims, any one of the claimed embodiments can be used in any combination.

The various component embodiments of this disclosure can be implemented in hardware, or in software modules running on one or more processors, or in combinations thereof. Those skilled in the art should understand that a microprocessor or digital signal processor (DSP) can be used in practice to implement some or all of the functions of some modules according to embodiments of the present disclosure. This disclosure can also be implemented as a device program (e.g., a computer program and a computer program product) for executing part or all of the methods described herein. Such a program for implementing this disclosure may be stored on a computer-readable medium or may take the form of one or more signals, and such signals can be downloaded from Internet websites, provided on carrier signals, or in any other form.

It should be noted that the above embodiments illustrate the present disclosure rather than limit it, and those skilled in the art can design alternative embodiments without departing from the scope of the appended claims. In the claims, any reference symbols located between parentheses should not be constructed as restrictions on the claims. This disclosure can be implemented by means of hardware comprising several different elements and by means of appropriately programmed computers. In the unit claims that list several devices, several of these devices may be embodied through the same hardware item. The use of words first, second, and third does not indicate any order. These words can be interpreted as names.

It should be understood that the terms used in this disclosure are only for the purpose of describing specific embodiments and are not intended to limit this disclosure.

It should also be understood that the term "and/or" used in this disclosure and the appended claims refers to any combination of one or more of the associated listed items and all possible combinations, and includes these combinations.

The above is only a specific implementation of this disclosure, however the protection scope of this disclosure is not limited thereto. Any skilled in the technical field can easily think of various equivalent modifications or replacements within the technical scope disclosed in this disclosure, and these modifications or replacements should be covered by the protection scope of this disclosure. Therefore, the protection scope of this disclosure shall be subject to the protection scope of the claims.

What is claimed is:

1. A defibrillation device, comprising:
a defibrillation component, configured to perform a defibrillation task;
a first processor, configured to acquire data from the defibrillation component and process said data to obtain defibrillation data; and
a second processor, configured to acquire extension device data from an extension device,
wherein the second processor is connected with the first processor, and the second processor and the first processor are capable of transmitting preset information,
wherein, when the first processor is in a working state, the second processor is capable of being switched from a turn-off state or a low power consumption state to a working state, or from the working state to the turn-off state or the low power consumption state;
wherein, when the first processor is in the working state, the first processor is capable of outputting the defibrillation data through a human-machine interaction component when the second processor is in the turn-off state or the low power consumption state;
wherein the processor state of the second processor is switched to the working state when
(1) at least one of the extension device, an extension function component, or an extension monitoring component satisfies a first extension start condition; or
(2) wherein the processor state of the second processor is switched to the working state according to a processor start instruction or an extension start instruction, wherein the processor start instruction or the extension start instruction is acquired through the human-machine interaction component,
wherein the processor start instruction is configured to control the second processor to switch to the working state, and the extension start instruction is configured to control the second processor to switch to the working state and to acquire the extension device data from the extension device corresponding to the extension start instruction; and
wherein,
when the second processor is in the working state, the second processor is further configured to transmit the acquired extension device data to the first processor; or
when the second processor is in the working state, the second processor is further configured to process the acquired extension device data and then transmit the processed extension device data to the first processor; or
when the second processor is in the working state, the first processor is configured to acquire an operation instruction for the extension device through a human-machine interaction component, and transmit the operation instruction for the extension device to the second processor, wherein the second processor is further configured to control the extension device to execute a corresponding extension task according to the operation instruction; or
when the second processor is in the working state, the first processor is configured to acquire an operation instruction for the extension device through a human-machine interaction component, and transmit the operation instruction for the extension device to the second processor, wherein the second processor is further configured to process the acquired extension device data from the extension device according to the operation instruction.

2. The defibrillation device according to claim 1, wherein, when the second processor is in the working state, the second processor acquires the extension device data from the extension device.

3. The defibrillation device according to claim 2, wherein the first processor is further configured to switch the processor state of the second processor; or
the second processor is further configured to switch the processor state of the second processor; or
the defibrillation device further comprises a third processor, configured to switch the processor state of the second processor.

4. The defibrillation device according to claim 3, wherein the processor state of the second processor is switched according to the defibrillation data or monitoring data;
wherein the monitoring data is obtained by the first processor, through processing data acquired from a monitoring component.

5. The defibrillation device according to claim 4, wherein the processor state of the second processor is switched to the working state when the defibrillation data or the monitoring data satisfies a preset second extension start condition.

6. The defibrillation device according to claim 1, wherein the human-machine interaction component is further configured to output indication information when the defibrillation data or monitoring data satisfies a preset indication condition,
wherein the indication information is configured to indicate a user to operate to trigger the processor start instruction or the extension start instruction; wherein the monitoring data is obtained by the first processor, through processing data which is acquired from a monitoring component.

7. The defibrillation device according to claim 1, wherein, when the second processor is in the turn-off state or the low power consumption state, the second processor stops acquiring the extension device data from the extension device.

8. The defibrillation device according to claim 7, wherein the processor state of the second processor is switched to the turn-off state or the low power consumption state, when at least one of the extension device, an extension function component, or an extension monitoring component satisfies a first extension turn-off condition, or, when the defibrillation data or monitoring data satisfies a preset second extension turn-off condition; or the processor state of the second processor is switched to the turn-off state or the low power consumption state according to a turn-off instruction, wherein the turn-off instruction is acquired through a human-machine interaction component.

9. The defibrillation device according to claim 1, wherein:

the defibrillation device further comprises a communication component;

the first processor is further configured to transmit the defibrillation data or monitoring data to the second processor; and when the second processor is in the working state, the second processor is further configured to transmit the defibrillation data or monitoring data to a target device through the communication component, or the second processor is further configured to transmit the acquired extension device data or processed extension device data to a target device through the communication component.

10. The defibrillation device according to claim 1, wherein:

the defibrillation device further comprises an ultrasonic device or a laryngoscope device; and the second processor is further configured to acquire ultrasonic data or laryngoscope data from the ultrasonic device or the laryngoscope device, wherein the ultrasonic data is ultrasonic image data, or the laryngoscope data is laryngoscope image data, wherein when the second processor is in the working state, the second processor is further configured to transmit the ultrasonic image data or the laryngoscope image data to the first processor, so as to display an ultrasonic image or a laryngoscope image through a human-machine interaction component; or the second processor is further configured to transmit the ultrasonic image data or the laryngoscope image data to a target device through a communication component; or when the second processor is in the working state, the second processor is further configured to process the ultrasonic data or the laryngoscope data to generate ultrasonic image data and laryngoscope image data, and the second processor is further configured to transmit the ultrasonic image data or the laryngoscope image data to the first processor, so as to display an ultrasonic image or a laryngoscope image through a human-machine interaction component, or transmit the ultrasonic image data or the laryngoscope image data to a target device through a communication component.

11. The defibrillation device according to claim 1, wherein the defibrillation device further comprises an extension function component connected with the second processor, wherein the extension function component comprises at least one of: a data reading component, an extension human-machine interaction component, or a camera component, wherein:

when the second processor is in the working state, the second processor is further configured to acquire the extension device data through at least one of the data reading component, the extension human-machine interaction component, or the camera component, and to transmit the extension device data to a target device or the first processor; or when the second processor is in the working state, the second processor is further configured to acquire feedback information for the extension device data, wherein, the feedback information is transmitted by a target device.

12. The defibrillation device according to claim 1, wherein the defibrillation device further comprises an extension monitoring component, wherein:

when the second processor is in the working state, the second processor is further configured to acquire data from the extension monitoring component and process said data; and when a second preset condition occurs, the second processor is further configured to acquire data from the defibrillation component or a monitoring component and process said data to obtain the defibrillation data or monitoring data.

13. The defibrillation device according to claim 1, wherein:

the defibrillation device thither comprises a power supply device, wherein a power supply terminal of the power supply device is connected with a power receiving terminal of the first processor and a power receiving terminal of the second processor, wherein an isolation circuit is provided between the power receiving terminal of the first processor and the power receiving terminal of the second processor, when a first preset condition occurs, the isolation circuit is configured to disconnect power supply to the second processor and meanwhile maintain power supply to the first processor; or the defibrillation device further comprises a power supply device, wherein the power supply device comprises a first power supply terminal and a second power supply terminal, wherein the first power supply terminal is connected with a power receiving terminal of the first processor, and the second power supply terminal is connected with a power receiving terminal of the second processor, wherein the power supply device further comprises a switching component connected with the first power supply terminal and the second power supply terminal, wherein, when a first preset condition occurs, the switching component is configured to disconnect from the second power supply terminal and meanwhile maintain connection with the first power supply terminal.

14. A defibrillation device, comprising:

a defibrillation component, configured to perform a defibrillation task;

at least two processors, comprising at least a first processor and a second processor, wherein, in a first state, the first processor is at least configured to acquire data from the defibrillation component, process said data to obtain defibrillation data, and at least generate at least one piece of basic display information based on the defibrillation data, and the second processor is at least configured to acquire data from at least one first extension device, process said data to obtain first extension device data, and generate at least one piece of first extension display information based on the first extension device data, wherein at least one processor of the at least two processors, comprises a display fusion module, wherein, in the first state, the display fusion module is configured to receive the at least one piece of basic display information generated by the first processor and the at least one piece of first extension display information generated by the second processor, and to fuse the at least one piece of basic display information and the at least one piece of first extension display information to generate terminal display information; and a display, configured to output the terminal display information, wherein the processor state of the second processor is switched to the working state when (1) at least one of the extension device, an extension function component, or an extension monitoring component satisfies a first extension start condition; or (2) wherein the processor state of the second processor is switched to the working state according to a processor start instruction or an extension start instruction, wherein the processor start instruction or the extension start instruction is acquired through the human-machine interaction component, wherein the processor start instruction is configured to control the second processor to switch to the working state, and the extension start instruction is configured to control the second processor to switch to the working state and to acquire the extension device data from the extension device corresponding to the extension start instruction.

15. The defibrillation device according to claim 14, wherein the defibrillation device further comprises a monitoring component configured to perform a monitoring task; and the first processor is further configured to acquire data from the monitoring component, process said data to obtain the monitoring data, and at least generate the at least one piece of basic display information based on the defibrillation data and the monitoring data.

16. The defibrillation device according to claim 15, wherein, to at least generate the at least one piece of basic display information based on the defibrillation data and the monitoring data, the first processor is further configured to generate defibrillation display information based on the defibrillation data, and generate monitoring display information based on the monitoring data; and the display fusion module is further configured to receive the defibrillation display information and the monitoring display information generated by the first processor, and fuse the defibrillation display information and the monitoring display information to generate the basic display information.

17. The defibrillation device according to claim 14, wherein the first processor is further configured to acquire second extension device data from at least one second extension device, and generate at least one piece of second extension display information based on the second extension device data; and the display fusion module is further configured to receive the at least one piece of second extension display information generated by the first processor, and fuse the at least one piece of basic display information, the at least one piece of first extension display information, and the at least one piece of second extension display information to generate the terminal display information.

18. The defibrillation device according to claim 14, wherein the first processor comprises the display fusion module and the first processor is further configured to transmit the terminal display information to the display; or the second processor comprises the display fusion module and the second processor is further configured to transmit the terminal display information to the display; or the at least two processors further comprise a third processor, wherein the third processor comprises the display fusion module and the third processor is configured to transmit the terminal display information to the display.

19. The defibrillation device according to claim 14, wherein:

in a second state, the first processor is further configured to acquire data from the defibrillation component and process said data to obtain the defibrillation data, but not generate the basic display information; or in a third state, the second processor is further configured to acquire data from the first extension device and process said data to obtain the first extension device data, but not generate the first extension display information.

20. The defibrillation device according to claim 14, wherein to fuse the at least one piece of basic display information and the at least one piece of first extension display information to generate terminal display information, the display fusion module is further configured to superimpose the at least one piece of basic display information and the at least one piece of first extension display information to generate the terminal display information; or the display fusion module is further configured to join the at least one piece of basic display information and the at least one piece of first extension display information to generate the terminal display information.

21. The defibrillation device according to claim 17, wherein to fuse the at least one piece of basic display information, the at least one piece of first extension display information and the at least one piece of second extension display information to generate the terminal display information, the display fusion module is further configured to superimpose the at least one piece of basic display information, the at least one piece of first extension display information, and the at least one piece of second extension display information to generate the terminal display information, or the display fusion module is further configured to join the at least one piece of basic display information, the at least one piece of first extension display information, and the at least one piece of second extension display information to generate the terminal display information.

22. The defibrillation device according to claim 14, wherein, in a fourth state, the display fusion module is further configured to fuse the at least one piece of basic display information and abnormal display information to generate the terminal display information, wherein the abnormal display information is configured to indicate that the at least one piece of first extension display information or at least one piece of second extension display information is abnormal, wherein the terminal display information comprises a basic display area which corresponds to the basic display information and an extension display area which corresponds to the extension display information, wherein, in the fourth state, the extension display area is configured to display the abnormal display information.

23. A medical device, comprising:

a basic component, configured to perform a basic medical function;

at least two processors, including a first processor and a second processor, at least configured to, in a first state, acquire data from the basic component, process said data to obtain basic data, and at least generate at least one piece of basic display information based on the basic data, and to acquire data from at least one first extension device, process said data to obtain first extension device data, and generate at least one piece of first extension display information based on the first extension device data;

the at least two processors comprise a display fusion module, wherein the display fusion module is configured to, in the first state, fuse the at least one piece of basic display information and at least one piece of extension display information to generate terminal display information, wherein the at least one piece of extension display information comprises the at least one piece of first extension display information, wherein the display fusion module is further configured to, in a fourth state, fuse the at least one piece of basic display information and abnormal display information to generate the terminal display information, wherein the abnormal display information is configured to indicate that the at least one piece of first extension display information is abnormal; and a display, configured to output the terminal display information, wherein the processor state of the second processor is switched to the working state when (1) at least one of the extension device, an extension function component, or an extension monitoring component satisfies a first extension start condition; or (2) wherein the processor state of the second processor is switched to the working state according to a processor start instruction or an extension start instruction, wherein the processor start instruction or the extension start instruction is acquired through the human-machine interaction component, wherein the processor start instruction is configured to control the second processor to switch to the working state, and the extension start instruction is configured to control the second processor to switch to the working state and to acquire the extension device data from the extension device corresponding to the extension start instruction.

24. The medical device according to claim 23, wherein the at least one processor comprises a first processor at least configured to:

acquire the data from the basic component, process said data to obtain the basic data, and at least generate the at least one piece of basic display information based on the basic data; and acquire the data from the at least one first extension device, process said data to obtain the first extension device data, and generate the at least one piece of first extension display information based on the first extension device data.

* * * * *